(12) United States Patent
Duffy et al.

(10) Patent No.: US 9,678,068 B2
(45) Date of Patent: Jun. 13, 2017

(54) ULTRA-SENSITIVE DETECTION OF MOLECULES USING DUAL DETECTION METHODS

(75) Inventors: David C. Duffy, Arlington, MA (US); David M. Rissin, Somerville, MA (US); David R. Walt, Boston, MA (US); Linan Song, Waltham, MA (US); Lei Chang, Winchester, MA (US)

(73) Assignee: Quanterix Corporation, Lexington, MA (US)

( * ) Notice: Subject to any disclaimer, the term of this patent is extended or adjusted under 35 U.S.C. 154(b) by 1512 days.

(21) Appl. No.: 12/731,135

(22) Filed: Mar. 24, 2010

(65) Prior Publication Data

US 2011/0212462 A1    Sep. 1, 2011

Related U.S. Application Data

(60) Provisional application No. 61/309,170, filed on Mar. 1, 2010.

(51) Int. Cl.
*G01N 33/543* (2006.01)
*G01N 33/53* (2006.01)

(52) U.S. Cl.
CPC ... *G01N 33/54393* (2013.01); *G01N 33/5306* (2013.01)

(58) Field of Classification Search
CPC .................. G01N 33/5306; G01N 33/54393
USPC ............................................. 436/518; 435/4
See application file for complete search history.

(56) References Cited

U.S. PATENT DOCUMENTS

| | | | |
|---|---|---|---|
| 3,212,986 A | 10/1965 | Pennington | |
| 3,712,986 A | 1/1973 | Collings | |
| 4,200,110 A | 4/1980 | Peterson et al. | |
| 4,232,119 A | 11/1980 | Carlsson et al. | |
| 4,631,211 A | 12/1986 | Houghten | |
| 4,780,421 A * | 10/1988 | Kameda ............... | C07D 493/10 435/968 |
| 4,883,642 A | 11/1989 | Bisconte | |
| 4,907,037 A | 3/1990 | Boisde et al. | |
| 4,924,870 A | 5/1990 | Wlodarczyk et al. | |
| 4,962,037 A | 10/1990 | Jett et al. | |
| 5,026,159 A | 6/1991 | Allen et al. | |
| 5,028,535 A | 7/1991 | Buechler et al. | |
| 5,089,391 A | 2/1992 | Buechler et al. | |
| 5,091,300 A | 2/1992 | Hurni et al. | |
| 5,108,961 A | 4/1992 | Zhong et al. | |
| 5,152,816 A | 10/1992 | Berkey | |
| 5,190,857 A | 3/1993 | Allen et al. | |
| 5,196,306 A | 3/1993 | Bobrow et al. | |
| 5,244,636 A | 9/1993 | Walt et al. | |
| 5,244,813 A | 9/1993 | Walt et al. | |
| 5,250,264 A | 10/1993 | Walt et al. | |
| 5,252,494 A | 10/1993 | Walt | |
| 5,298,741 A | 3/1994 | Walt et al. | |
| 5,315,375 A | 5/1994 | Allen | |
| 5,320,814 A | 6/1994 | Walt et al. | |
| 5,329,461 A | 7/1994 | Allen et al. | |
| 5,374,395 A | 12/1994 | Robinson et al. | |
| 5,405,783 A | 4/1995 | Pirrung et al. | |
| 5,445,934 A | 8/1995 | Fodor et al. | |
| 5,468,846 A | 11/1995 | Ichikawa et al. | |
| 5,488,567 A | 1/1996 | Allen et al. | |
| 5,512,490 A | 4/1996 | Walt et al. | |
| 5,532,138 A | 7/1996 | Singh et al. | |
| 5,532,379 A | 7/1996 | Fujimoto | |
| 5,545,531 A | 8/1996 | Rava et al. | |
| 5,583,001 A | 12/1996 | Bobrow et al. | |
| 5,620,850 A | 4/1997 | Bamdad et al. | |
| 5,633,972 A | 5/1997 | Walt et al. | |
| 5,690,894 A | 11/1997 | Pinkel et al. | |
| 5,700,637 A | 12/1997 | Southern | |
| 5,731,158 A | 3/1998 | Bobrow et al. | |
| 5,770,455 A | 6/1998 | Cargill et al. | |
| 5,807,522 A | 9/1998 | Brown et al. | |
| 5,814,524 A | 9/1998 | Walt et al. | |
| 5,885,529 A * | 3/1999 | Babson ............... | B01L 3/50853 134/150 |
| 5,900,481 A | 5/1999 | Lough et al. | |
| 5,981,180 A | 11/1999 | Chandler et al. | |
| 6,001,564 A | 12/1999 | Bergeron et al. | |
| 6,007,690 A | 12/1999 | Nelson et al. | |
| 6,013,445 A | 1/2000 | Albrecht et al. | |
| 6,023,540 A | 2/2000 | Walt et al. | |
| 6,133,436 A | 10/2000 | Koster et al. | |
| 6,143,496 A | 11/2000 | Brown et al. | |
| 6,156,270 A | 12/2000 | Buechler | |
| 6,174,695 B1 | 1/2001 | Hammock et al. | |
| 6,210,910 B1 | 4/2001 | Walt et al. | |
| 6,266,459 B1 | 7/2001 | Walt et al. | |
| 6,285,807 B1 | 9/2001 | Walt et al. | |

(Continued)

FOREIGN PATENT DOCUMENTS

| | | |
|---|---|---|
| AU | 199956253 B2 | 3/2000 |
| CN | 1635146 A | 7/2005 |
| CN | 1950520 A | 4/2007 |
| DE | 19540098 A1 | 4/1997 |
| EP | 0 805 215 A2 | 11/1997 |

(Continued)

OTHER PUBLICATIONS

Invitation to Pay Additional Fees for PCT/US2009/005250 mailed Feb. 12, 2010.

(Continued)

*Primary Examiner* — Ann Lam
(74) *Attorney, Agent, or Firm* — Finch & Maloney PLLC

(57) ABSTRACT

Described herein are systems and methods for the detection of and/or determination of a measure of the concentration of analyte molecules or particles in a fluid sample. In some cases, the systems and methods employ techniques to reduce or limit the negative effects associated with non-specific binding events. Certain methods of the present invention involve associating the analyte molecules at least a first type of binding ligand and at least a second type of binding ligand, and spatially segregating the analyte molecules into a plurality of locations on a surface. The presence of an analyte molecule at or in a location may be determined by determining the presence of both the first type of binding ligand and the second type of binding ligand.

30 Claims, 6 Drawing Sheets

(56) References Cited

U.S. PATENT DOCUMENTS

| | | |
|---|---|---|
| 6,327,410 B1 | 12/2001 | Walt et al. |
| 6,329,139 B1 | 12/2001 | Nova et al. |
| 6,368,874 B1 | 4/2002 | Gallop et al. |
| 6,377,721 B1 | 4/2002 | Walt et al. |
| 6,388,746 B1 | 5/2002 | Eriksson et al. |
| 6,396,995 B1 | 5/2002 | Stuelpnagel et al. |
| 6,406,845 B1 | 6/2002 | Walt et al. |
| 6,432,630 B1 | 8/2002 | Blankenstein |
| 6,482,593 B2 | 11/2002 | Walt et al. |
| 6,582,908 B2 | 6/2003 | Fodor et al. |
| 6,602,702 B1 | 8/2003 | McDevitt et al. |
| 6,620,584 B1 | 9/2003 | Chee et al. |
| 6,635,452 B1 | 10/2003 | Monforte et al. |
| 6,667,159 B1 | 12/2003 | Walt et al. |
| 6,713,309 B1 | 3/2004 | Anderson et al. |
| 6,714,303 B2 | 3/2004 | Ivarsson |
| 6,821,449 B2 | 11/2004 | Caplen et al. |
| 6,838,051 B2 | 1/2005 | Marquiss et al. |
| 6,858,394 B1 | 2/2005 | Chee et al. |
| 6,859,570 B2 | 2/2005 | Walt |
| 6,878,345 B1 | 4/2005 | Astle |
| 6,929,924 B2 | 8/2005 | Bouanani et al. |
| 6,942,968 B1 | 9/2005 | Dickinson et al. |
| 6,943,034 B1 | 9/2005 | Winkler et al. |
| 6,991,939 B2 | 1/2006 | Walt et al. |
| 6,999,657 B2 | 2/2006 | Walt |
| 7,056,746 B2 | 6/2006 | Seul et al. |
| 7,060,431 B2 | 6/2006 | Chee et al. |
| 7,115,884 B1 | 10/2006 | Walt et al. |
| 7,211,390 B2 | 5/2007 | Rothberg et al. |
| 7,244,559 B2 | 7/2007 | Rothberg et al. |
| 7,250,267 B2 | 7/2007 | Walt et al. |
| 7,264,929 B2 | 9/2007 | Rothberg et al. |
| 7,348,181 B2 | 3/2008 | Walt et al. |
| 7,480,433 B2 | 1/2009 | Walt et al. |
| 7,572,581 B2 | 8/2009 | Gelfand et al. |
| 7,651,841 B2 | 1/2010 | Song et al. |
| 7,759,062 B2 | 7/2010 | Allawi et al. |
| 7,776,553 B2 | 8/2010 | Love et al. |
| 7,838,250 B1 | 11/2010 | Goix et al. |
| 8,222,047 B2 * | 7/2012 | Duffy ............... G01N 33/54326 436/518 |
| 8,236,574 B2 * | 8/2012 | Duffy ............... G01N 33/54306 436/518 |
| 8,415,171 B2 * | 4/2013 | Rissin ................ G01N 33/50 436/518 |
| 8,460,878 B2 | 6/2013 | Walt et al. |
| 8,460,879 B2 | 6/2013 | Walt et al. |
| 8,492,098 B2 | 7/2013 | Walt et al. |
| 8,846,415 B2 * | 9/2014 | Duffy ............... G01N 33/54326 436/518 |
| 9,110,025 B2 * | 8/2015 | Rissin ................ G01N 21/6452 |
| 9,310,360 B2 * | 4/2016 | Duffy ............... G01N 33/54306 |
| 2002/0009391 A1 | 1/2002 | Marquiss et al. |
| 2002/0090650 A1 | 7/2002 | Empedocles et al. |
| 2002/0122612 A1 | 9/2002 | Walt et al. |
| 2003/0027126 A1 | 2/2003 | Walt et al. |
| 2003/0091475 A1 | 5/2003 | Yu et al. |
| 2003/0104361 A1 * | 6/2003 | Weininger .......... C12Q 1/6804 435/6.15 |
| 2003/0143580 A1 * | 7/2003 | Straus ............. G01N 33/56916 435/6.1 |
| 2003/0198573 A1 | 10/2003 | Forood et al. |
| 2004/0038426 A1 | 2/2004 | Manalis |
| 2004/0043502 A1 | 3/2004 | Song et al. |
| 2004/0053322 A1 | 3/2004 | McDevitt et al. |
| 2004/0071599 A1 | 4/2004 | Rusch et al. |
| 2004/0072278 A1 | 4/2004 | Chou et al. |
| 2004/0086426 A1 | 5/2004 | Vann et al. |
| 2004/0101918 A1 | 5/2004 | Cauci |
| 2004/0142386 A1 | 7/2004 | Rigler et al. |
| 2004/0248325 A1 * | 12/2004 | Bukusoglu ......... G01N 33/5088 436/548 |
| 2004/0253624 A1 | 12/2004 | Smith et al. |
| 2004/0259237 A1 | 12/2004 | Kellogg et al. |
| 2005/0112634 A1 | 5/2005 | Woudenberg et al. |
| 2005/0112655 A1 | 5/2005 | Banerjee et al. |
| 2005/0130173 A1 | 6/2005 | Leamon et al. |
| 2005/0130188 A1 | 6/2005 | Walt et al. |
| 2005/0131650 A1 | 6/2005 | Andersson et al. |
| 2005/0164289 A1 | 7/2005 | Quate et al. |
| 2005/0221281 A1 | 10/2005 | Ho |
| 2005/0226780 A1 | 10/2005 | Sandell et al. |
| 2005/0244308 A1 | 11/2005 | Tanaami et al. |
| 2005/0266433 A1 | 12/2005 | Kapur et al. |
| 2006/0006067 A1 | 1/2006 | Unger |
| 2006/0013543 A1 | 1/2006 | Walt et al. |
| 2006/0040297 A1 | 2/2006 | Leamon et al. |
| 2006/0068409 A1 | 3/2006 | Phan et al. |
| 2006/0078998 A1 | 4/2006 | Puskas et al. |
| 2006/0084183 A1 | 4/2006 | Henricksen |
| 2006/0139635 A1 | 6/2006 | Kersey et al. |
| 2007/0040095 A1 | 2/2007 | Walt et al. |
| 2007/0059754 A1 * | 3/2007 | Kordunsky et al. ............. 435/6 |
| 2007/0074972 A1 | 4/2007 | Nassef et al. |
| 2007/0116607 A1 | 5/2007 | Wang et al. |
| 2007/0259381 A1 | 11/2007 | Walt et al. |
| 2007/0259385 A1 | 11/2007 | Walt et al. |
| 2007/0259448 A1 | 11/2007 | Walt et al. |
| 2008/0032324 A1 | 2/2008 | Walt et al. |
| 2008/0064113 A1 | 3/2008 | Goix |
| 2008/0269069 A1 | 10/2008 | Bacher et al. |
| 2009/0036324 A1 | 2/2009 | Fan et al. |
| 2009/0087860 A1 | 4/2009 | Todd et al. |
| 2009/0142755 A1 | 6/2009 | Albitar |
| 2009/0149341 A1 | 6/2009 | Walt et al. |
| 2009/0156425 A1 | 6/2009 | Walt et al. |
| 2009/0170728 A1 | 7/2009 | Walt et al. |
| 2009/0239308 A1 | 9/2009 | Dube et al. |
| 2009/0254180 A1 | 10/2009 | Pazanowski |
| 2009/0289834 A1 | 11/2009 | Devensky |
| 2009/0307772 A1 | 12/2009 | Markham |
| 2010/0075355 A1 | 3/2010 | Duffy et al. |
| 2010/0075407 A1 | 3/2010 | Duffy et al. |
| 2010/0075439 A1 * | 3/2010 | Duffy ............... G01N 33/54306 436/518 |
| 2010/0075862 A1 | 3/2010 | Duffy et al. |
| 2010/0140289 A1 | 6/2010 | Knobel et al. |
| 2010/0189338 A1 | 7/2010 | Lin et al. |
| 2010/0192573 A1 | 8/2010 | Hamilton et al. |
| 2010/0204335 A1 | 8/2010 | Beddingfield et al. |
| 2010/0227379 A1 | 9/2010 | Wo et al. |
| 2011/0183270 A1 | 7/2011 | Lo et al. |
| 2011/0195852 A1 | 8/2011 | Walt et al. |
| 2011/0212537 A1 | 9/2011 | Duffy et al. |
| 2011/0212848 A1 | 9/2011 | Duffy et al. |
| 2011/0245097 A1 | 10/2011 | Rissin et al. |
| 2012/0196774 A1 | 8/2012 | Fournier et al. |
| 2012/0214160 A1 | 8/2012 | Deng et al. |
| 2012/0277114 A1 | 11/2012 | Duffy et al. |
| 2012/0289428 A1 | 11/2012 | Duffy et al. |
| 2013/0165342 A1 | 6/2013 | Rissin et al. |
| 2013/0345078 A1 | 12/2013 | Walt et al. |
| 2014/0094386 A1 | 4/2014 | Wilson et al. |
| 2014/0227720 A1 | 8/2014 | Wilson et al. |
| 2014/0302532 A1 | 10/2014 | Wilson et al. |
| 2015/0355182 A1 * | 12/2015 | Rissin ................ G01N 21/6452 506/9 |

FOREIGN PATENT DOCUMENTS

| | | |
|---|---|---|
| EP | 1 180 679 A1 | 2/2002 |
| EP | 1 259 810 B1 | 11/2006 |
| EP | 1 721 657 A1 | 11/2006 |
| EP | 2 267 451 A2 | 12/2010 |
| JP | 2001/269196 A | 10/2001 |
| JP | 2002-506200 A | 2/2002 |
| JP | 2002-525587 A | 8/2002 |
| JP | 2002-526743 A | 8/2002 |
| JP | 2004-354164 A | 12/2004 |
| JP | 2005-518553 A | 6/2005 |
| JP | 2006-511792 A | 4/2006 |

(56) References Cited

FOREIGN PATENT DOCUMENTS

| WO | WO 88/05533 A1 | 7/1988 |
|---|---|---|
| WO | WO 93/06121 A1 | 4/1993 |
| WO | WO 93/24517 A2 | 12/1993 |
| WO | WO 95/25116 A1 | 9/1995 |
| WO | WO 95/32425 A1 | 11/1995 |
| WO | WO 95/35506 A2 | 12/1995 |
| WO | WO 97/27326 A1 | 7/1997 |
| WO | WO 98/50782 A2 | 11/1998 |
| WO | WO 99/45357 A2 | 9/1999 |
| WO | WO 99/58948 A2 | 11/1999 |
| WO | WO 00/04372 A1 | 1/2000 |
| WO | WO 00/47996 A2 | 8/2000 |
| WO | WO 01/57520 A2 | 8/2001 |
| WO | WO 03/054142 A2 | 7/2003 |
| WO | WO 03/073817 A1 | 9/2003 |
| WO | WO 2004/065000 A1 | 8/2004 |
| WO | WO 2004/083443 A1 | 9/2004 |
| WO | WO 2005/019419 A2 | 3/2005 |
| WO | WO 2005/023414 A1 | 3/2005 |
| WO | WO 2005/033283 A2 | 4/2005 |
| WO | WO 2005/054431 A2 | 6/2005 |
| WO | WO 2006/007726 A1 | 1/2006 |
| WO | WO 2006/055739 A2 | 5/2006 |
| WO | WO 2006/078289 A2 | 7/2006 |
| WO | WO 2006/102297 A1 | 9/2006 |
| WO | WO 2006/108180 A2 | 10/2006 |
| WO | WO 2007/044091 A2 | 4/2007 |
| WO | WO 2007/044974 A2 | 4/2007 |
| WO | WO 2007/081385 A2 | 7/2007 |
| WO | WO 2007/081386 A2 | 7/2007 |
| WO | WO 2007/081387 A1 | 7/2007 |
| WO | WO 2007/084192 A2 | 7/2007 |
| WO | WO 2007/098148 A2 | 8/2007 |
| WO | WO 2007/114947 A2 | 10/2007 |
| WO | WO 2008/048371 A2 | 4/2008 |
| WO | WO 2009/029073 A1 | 3/2009 |
| WO | WO 2010/039180 A2 | 4/2010 |
| WO | WO 2011/109372 A1 | 9/2011 |

OTHER PUBLICATIONS

Invitation to Pay Additional Fees for PCT/US2009/005248 mailed Jan. 21, 2010.

International Preliminary Report on Patentability for PCT/US2011/026645 mailed Sep. 13, 2012.

International Preliminary Report on Patentability for PCT/US2011/026657 mailed Sep. 13, 2012.

International Preliminary Report on Patentability for PCT/US2011/026665 mailed Sep. 13, 2012.

International Search Report and Written Opinion for PCT/US2012/022923 mailed Jun. 25, 2012.

Notice of Allowance for U.S. Appl. No. 12/236,486, filed Sep. 23, 2008, published as US 2010-0075407 on Mar. 25, 2010, which Notice of Allowance is dated Mar. 22, 2012, and allowed claims for U.S. Appl. No. 12/236,486 as of Mar. 22, 2012.

Office Action for U.S. Appl. No. 12/731,130, filed Mar. 24, 2010, published as US 2011-0212848 on Sep. 1, 2011, which Office Action is dated Mar. 28, 2012, and claims as pending for U.S. Appl. No. 12/731,130 as of Mar. 28, 2012.

Notice of Allowance for U.S. Appl. No. 12/731,130, filed Mar. 24, 2010, published as US 2011-0212848 on Sep. 1, 2011, which Notice of Allowance is dated Jun. 1, 2012, and allowed claims for U.S. Appl. No. 12/731,130 as of Jun. 1, 2012.

Office Action for U.S. Appl. No. 12/731,136, filed Mar. 24, 2010, published as US 2011-0212537 on Sep. 1, 2011, which Office Action is dated Jun. 15, 2012, and claims as pending for U.S. Appl. No. 12/731,136 as of Jun. 15, 2012.

Office Action for U.S. Appl. No. 11/707,385, filed Feb. 16, 2007, published as US 2007-0259448 on Nov. 8, 2007, which Office Action is dated Sep. 27, 2012, and claims as pending for U.S. Appl. No. 11/707,385 as of Sep. 27, 2012.

Office Action for U.S. Appl. No. 11/707,383, filed Feb. 16, 2007, published as US 2007-0259385 on Nov. 8, 2007, which Office Action is dated Sep. 27, 2012, and claims as pending for U.S. Appl. No. 11/707,383 as of Sep. 27, 2012.

Office Action for U.S. Appl. No. 11/707,384, filed Feb. 16, 2007, published as US 2007-0259381 on Nov. 8, 2007, which Office Action is dated Sep. 27, 2012, and claims as pending for U.S. Appl. No. 11/707,384 as of Sep. 27, 2012.

Beer et al., On-chip, real-time, single-copy polymerase chain reaction in picoliter droplets. Anal Chem. Nov. 15, 2007;79(22):8471-5. Epub Oct. 11, 2007. Abstract only.

Hindson et al., High-throughput droplet digital PCR system for absolute quantitation of DNA copy number. Anal Chem. Nov. 15, 2011;83(22):8604-10. Epub Oct. 28, 2011.

Hirano et al., A novel method for DNA molecular counting. Nucleic Acids Symp Ser. 2000;(44):157-8.

Kiss et al., High-throughput quantitative polymerase chain reaction in picoliter droplets. Anal Chem. Dec. 1, 2008;80(23):8975-81.

Morrison et al., Nanoliter high throughput quantitative PCR. Nucleic Acids Res. 2006;34(18):e123. Epub Sep. 25, 2006.

Warren et al., Transcription factor profiling in individual hematopoietic progenitors by digital RT-PCR. Proc Natl Acad Sci U S A. Nov. 21, 2006;103(47):17807-12. Epub Nov. 10, 2006.

Vogelstein et al., Digital PCR. Proc Natl Acad Sci U S A. Aug. 3, 1999;96(16):9236-41.

European Search Report for European Application No. 07751131.9, mailed Sep. 8, 2009.

International Search Report and Written Opinion for International Application No. PCT/US2007/004349, mailed Aug. 21, 2008.

International Preliminary Report on Patentability, Chapter 1, for International Application No. PCT/US2007/004349 dated Sep. 25, 2008.

International Preliminary Report on Patentability, Chapter 2, for International Application No. PCT/US2007/004349 dated Mar. 23, 2009.

International Search Report and Written Opinion for International Application No. PCT/US2007/019184, mailed Jun. 19, 2008.

International Preliminary Report on Patentability, Chapter 1, for International Application No. PCT/US2007/019184, mailed Mar. 11, 2010.

International Search Report and Written Opinion for International Application No. PCT/US2009/005248, mailed Mar. 1, 2010.

International Preliminary Report on Patentability, Chapter 1, for International Application No. PCT/US2009/005248, mailed Apr. 7, 2011.

International Search Report and Written Opinion for International Application No. PCT/US2009/005250, mailed Mar. 22, 2010.

International Preliminary Report on Patentability, Chapter 1, for International Application No. PCT/US2009/005250, mailed Apr. 7, 2011.

International Search Report and Written Opinion for International Application No. PCT/US2011/026645, mailed Nov. 24, 2011.

International Search Report and Written Opinion for International Application No. PCT/US2011/026657, mailed May 24, 2011.

International Search Report and Written Opinion for International Application No. PCT/US2011/026665, mailed Jul. 5, 2011.

Office Action for U.S. Appl. No. 11/707,383, filed Feb. 16, 2007, published as US 2007-0259385 on Nov. 8, 2007, which Office Action is dated Mar. 16, 2009, and claims as pending for U.S. Appl. No. 11/707,383 as of Mar. 16, 2009.

Office Action for U.S. Appl. No. 11/707,383, filed Feb. 16, 2007, published as US 2007-0259385 on Nov. 8, 2007, which Office Action is dated Nov. 27, 2009, and claims as pending for U.S. Appl. No. 11/707,383 as of Nov. 27, 2009.

Office Action for U.S. Appl. No. 11/707,384, filed Feb. 16, 2007, published as US 2007-0259381 on Nov. 8, 2007, which Office Action is dated Mar. 16, 2009, and claims as pending for U.S. Appl. No. 11/707,384 as of Mar. 16, 2009.

Office Action for U.S. Appl. No. 11/707,384, filed Feb. 16, 2007, published as US 2007-0259381 on Nov. 8, 2007, which Office Action is dated Dec. 2, 2009, and claims as pending for U.S. Appl. No. 11/707,384 as of Dec. 2, 2009.

(56) References Cited

OTHER PUBLICATIONS

Office Action for U.S. Appl. No. 11/707,385, filed Feb. 16, 2007, published as US 2007-0259448 on Nov. 8, 2007, which Office Action is dated Mar. 16, 2009, and claims as pending for U.S. Appl. No. 11/707,385 as of Mar. 16, 2009.
Office Action for U.S. Appl. No. 11/707,385, filed Feb. 16, 2007, published as US 2007-0259448 on Nov. 8, 2007, which Office Action is dated Jan. 26, 2010, and claims as pending for U.S. Appl. No. 11/707,385 as of Jan. 26, 2010.
Office Action for U.S. Appl. No. 12/236,484, filed Sep. 23, 2008, published as US 2010-0075862 on Mar. 25, 2010, which Office Action is dated Sep. 9, 2010, and claims as pending for U.S. Appl. No. 12/236,484 as of Sep. 9, 2010.
Office Action for U.S. Appl. No. 12/236,484, filed Sep. 23, 2008, published as US 2010-0075862 on Mar. 25, 2010, which Office Action is dated Apr. 13, 2011, and claims as pending for U.S. Appl. No. 12/236,484 as of Apr. 13, 2011.
Office Action for U.S. Appl. No. 12/236,486, filed Sep. 23, 2008, published as US 2010-0075407 on Mar. 25, 2010, which Office Action is dated Nov. 23, 2011, and claims as pending for U.S. Appl. No. 12/236,486 as of Nov. 23, 2011.
Office Action for U.S. Appl. No. 12/236,488, filed Sep. 23, 2008, published as US 2010-0075439 on Mar. 25, 2010, which Office Action is dated Aug. 2, 2010, and claims as pending for U.S. Appl. No. 12/236,488 as of Aug. 2, 2010.
[No Author Listed] Novel test following prostate surgery could detect cancer recurrence earlier. AACR Press Release. Sep. 29, 2010. Last accessed at http://www.aacr.org/home/public--media/aacr-press-releases.aspx?d=2072 on Jan. 31, 2012. 2 pages.
[No Author Listed] Quanterix corporation awarded $185,000 grant from the National Cancer Institute. Quanterix Press Release. Sep. 30, 2008. Last accessed at http://www.quanterix.com/news/pressReleases/SBIR1Grant.html on Jan. 31, 2012. 1 page.
[No Author Listed] Quanterix corporation raises $15 million in series A financing. Quanterix Press Release. Aug. 25, 2008. Last accessed at http://www.quanterix.com/news/pressReleases/seriesAFunding.html on Jan. 31, 2012. 2 pages.
[No Author Listed] Single molecule arrays for digital detection in complex samples. Quanterix Corporation. IQT Technology Focus Day. Mar. 25, 2010. PowerPoint presentation. 30 pages.
Adams et al., Encoded fiber-optic microsphere arrays for probing protein-carbohydrate interactions. Angewandte Chemie. 2003; 115:5475-5478.
Agrawal et al., Nanometer-scale mapping and single-molecule detection with color-coded nanoparticle probes. Proc Natl Acad Sci U S A. Mar. 4, 2008;105(9):3298-303. Epub Feb. 27, 2008.
Agrawal et al., Single-bead immunoassays using magnetic microparticles and spectral-shifting quantum dots. J Agric Food Chem. May 16, 2007; 55(10):3778-82. Epub Apr. 25, 2007.
Ahn et al., Detection of *Salmonella* spp. Using microsphere-based, fiber-optic DNA microarrays. Anal Chem. Aug. 1, 2005; 77(15):5041-7.
Ahn et al., Fiber-optic microarray for simultaneous detection of multiple harmful algal bloom species. Appl Environ Microbiol. Sep. 2006; 72(9):5742-9.
Albert et al., Automatic decoding of sensor types within randomly ordered, high-density optical sensor arrays. Anal Bioanal Chem. Apr. 2002; 373(8):792-802. Epub Jul. 27, 2002.
Albert et al., Cross-reactive chemical sensor arrays. Chem Rev. Jul. 12, 2000; 100(7):2595-626.
Albert et al., Information coding in artificial olfaction multisensor arrays. Anal Chem. Aug. 15, 2003; 75(16):4161-7.
Albert et al., Optical multibead arrays for simple and complex odor discrimination. Anal Chem. Jun. 1, 2001; 73(11):2501-8.
Angenendt et al., Subnanoliter enzymatic assays on microarrays. Proteomics. Feb. 2005;5(2):420-5.
Arnaud, Observing single enzymes at work. Chemical & Engineering News. Oct. 2007; 85(44): 8.
Bencic-Nagale et al., Extending the longevity of fluorescence-based sensor arrays using adaptive exposure. Anal Chem. Oct. 1, 2005; 77(19):6155-62.
Bhat et al., Single molecule detection in nanofluidic digital array enables accurate measurement of DNA copy number. Anal Bioanal Chem. May 2009;394(2):457-67. Epub Mar. 15, 2009.
Biran et al., Optical imaging fiber-based live bacterial cell array biosensor. Anal Biochem. Apr. 1, 2003; 315(1):106-13.
Biran et al., Optical imaging fiber-based single live cell arrays: a high-density cell assay platform. Anal Chem. Jul. 1, 2002; 74(13):3046-54.
Blake et al., Phenotypic consequences of promoter-mediated transcriptional noise. Mol Cell. Dec. 28, 2006; 24(6):853-65.
Blicharz et al., Detection of inflammatory cytokines using a fiber optic microsphere immunoassay array. *Proc. SPIE.* 2006; 6380, 638010-1-638010-6.
Blicharz et al., Use of colorimetric test strips for monitoring the effect of hemodialysis on salivary nitrite and uric acid in patients with end-stage renal disease: a proof of principle. Clin Chem. Sep. 2008; 54(9):1473-80. Epub Aug. 1, 2008.
Bourzac, Next-generation diagnostics: a startup can detect tiny traces of cancer markers in blood samples. Technol Rev. May 13, 2008. Last accessed at http://www.technologyreview.com/Biztech/20760/?a=f on Feb. 2, 2012. 2 pages.
Bowden et al., Development of a microfluidic platform with an optical imaging microarray capable of attomolar target DNA detection. Anal Chem. Sep. 1, 2005; 77(17):5583-8. Epub Aug. 4, 2005.
Boyden, The chemotactic effect of mixtures of antibody and antigen on polymorphonuclear leucocytes. J Exp Med. Mar. 1, 1962;115:453-66.
Brehm-Stecher et al., Single-cell microbiology: tools, technologies, and applications. Microbiol Mol Biol Rev. Sep. 2004; 68(3):538-59.
Brogan et al., Optical fiber-based sensors: application to chemical biology. Curr Opin Chem Biol. Oct. 2005; 9(5):494-500. Epub Aug. 24, 2005.
Bronk et al., Combined imaging and chemical sensing using a single optical imaging fiber. Anal Chem. Sep. 1, 1995; 67(17):2750-7.
Bronk et al., Fabrication of patterned sensor arrays with aryl azides on a polymer-coated imaging optical fiber bundle. Anal Chem. Oct. 15, 1994; 66(20):3519-20.
Burton et al., A microfluidic chip-compatible bioassay based on single-molecule detection with high sensitivity and multiplexing. Lab Chip. Apr. 7, 2010; 10(7):843-51. Epub Jan. 14, 2010.
Campian, Colored and fluorescent solid supports. Innovation and Perspectives in Solid Phase Synthesis. Ed. R. Epton, Mayflower Worldwide Limited, Birmingham. Ch. 77. 1994:469-472.
Chen et al., Microfabricated arrays of cylindrical wells facilitate single-molecule enzymology of alpha-chymotrypsin. Biotechnol Prog. Jul.-Aug. 2009; 25(4):929-37.
Chin et al., Editor's Choice: Distinctive individualism. Science. Apr. 4, 2008;320:21.
Chon et al., Characterization of single-cell migration using a computer-aided fluorescence time-lapse videomicroscopy system. Anal Biochem. Oct. 15, 1997;252(2):246-54.
Deutsch et al., Apparatus for high-precision repetitive sequential optical measurement of living cells. Cytometry. Jul. 1, 1994; 16(3):214-26.
Dicesare et al., Individual cell migration analysis using fiber-optic bundles. Anal Bioanal Chem. May 2005; 382(1):37-43. Epub Apr. 1, 2005.
Dickinson et al., A chemical-detecting system based on a cross-reactive optical sensor array. Nature. Aug. 22, 1996; 382(6593):697-700.
Dickinson et al., Convergent, self-encoded bead sensor arrays in the design of an artificial. Anal Chem: Jun. 1, 1999; 71(11):2192-8.
Dickinson et al., Current trends in 'artificial-nose' technology: Trends Biotechnol. Jun. 1998; 16(6):250-8.
Egner et al., Tagging in combinatorial chemistry: the use of coloured and fluorescent beads. Chem Commun. 1997; 735-736.
Eid et al., Real-time DNA sequencing from single polymerase molecules. Science. Jan. 2, 2009; 323(5910):133-8. Epub Nov. 20, 2008.

(56) References Cited

OTHER PUBLICATIONS

Ekins et al., Single-molecule ELISA. Clin Chem. Mar. 2011;57(3):372-5. Epub Oct. 13, 2010. Papers in press. Oct. 13, 2010. pp. 1-3.
English et al., Ever-fluctuating single enzyme molecules: Michaelis-Menten equation revisited. Nat Chem Biol. Feb. 2006; 2(2):87-94. Epub Dec. 25, 2005.
Epstein et al., Combinatorial decoding: an approach for universal DNA array fabrication. J Am Chem Soc. Nov. 12, 2003; 125(45):13753-9.
Epstein et al., Fluorescence-based nucleic acid detection and microarrays. Analytica Chimica Acta. 2002; 469:3-36.
Epstein et al., High-density fiber-optic genosensor microsphere array capable of zeptomole detection limits. Anal Chem. Apr. 15, 2002; 74(8):1836-40.
Epstein et al., High-density, microsphere-based fiber optic DNA microarrays. Biosens Bioelectron. May 2003; 18(5-6):541-6.
Epstein, et al., Fluorescence-based fibre optic arrays: a universal platform for sensing. Chem Soc Rev. Jul. 2003; 32(4):203-14.
Ferguson et al., A fiber-optic DNA biosensor microarray for the analysis of gene expression. Nat Biotechnol. Dec. 1996; 14(13):1681-4.
Ferguson et al., High-density fiber-optic DNA random microsphere array. Anal Chem. Nov. 15, 2000; 72(22):5618-24.
Ferguson et al., Simultaneous monitoring of pH, $CO_2$ and $O_2$ using an optical imaging fiber. Analytica Chimica Acta. 1997; 340(1-3):123-131.
Fister et al., Counting single chromophore molecules for ultrasensitive analysis and separations on microchip devices. Analytical Chemistry. 1998; 70:431-437.
Fulton et al., Advanced multiplexed analysis with the FlowMetrix system. Clin Chem. Sep. 1997; 43(9):1749-56.
Furka et al., General method for rapid synthesis of multicomponent peptide mixtures. Int J Pept Protein Res. Jun. 1991;37(6):487-93.
Gebel, Molecule counting made easy. Anal Chem. Sep. 1, 2009; 7130-7131.
Giaever et al., Micromotion of mammalian cells measured electrically. Proc Natl Acad Sci U S A. Sep. 1, 1991;88(17):7896-900.
Gorris et al., Analytical chemistry on the femtoliter scale. Angew Chem Int Ed. 2010; 49:2-18.
Gorris et al., Mechanistic aspects of horseradish peroxidase elucidated through single-molecule studies. J Am Chem Soc. May 6, 2009; 131(17):6277-82.
Gorris et al., Optical-fiber bundles. FEBS J. Nov. 2007; 274(21):5462-70. Epub Oct. 12, 2007.
Gorris et al., Stochastic inhibitor release and binding from single-enzyme molecules. Proc Natl Acad Sci U S A. Nov. 6, 2007; 104(45):17680-5. Epub Oct. 26, 2007.
Härma et al., Europium nanoparticles and time-resolved fluorescence for ultrasensitive detection of prostate-specific antigen. Clin Chem. Mar. 2001; 47(3):561-8.
Härma et al., Miniature single-particle immunoassay for prostate-specific antigen in serum using recombinant Fab fragments. Clin Chem. Nov. 2000; 46(11):1755-61.
Härma et al., Zeptomole detection sensitivity of prostate-specific antigen in a rapid microtitre plate assay using time-resolved fluorescence. Luminescence. Nov.-Dec. 2000;15(6):351-5.
Hashida et al., Immune complex transfer enzyme immunoassay that is more sensitive and specific than western blotting for detection of antibody immunoglobulin G to human immunodeficiency virus type 1 in serum with recombinant pol and gag proteins as antigens. Clin Diagn Lab Immunol. Sep. 1995; 2(5):535-41.
Haugland, Handbook: A Guide to Fluorescent Probes and Labeling Technologies. Invitrogen, Eugene, OR. Molecular Probes, US. pp. 473-538.
He et al., Selective encapsulation of single cells and subcellular organelles into picoliter- and femtoliter-volume droplets. Anal Chem. Mar. 15, 2005; 77(6):1539-44.
Healey et al., Fiberoptic DNA sensor array capable of detecting point mutations. Anal Biochem. Sep. 5, 1997; 251(2):270-9.
Healey et al., Multianalyte biosensors on optical imaging bundles. Bicisens Bioelectron. 1997; 12(6):521-9.
Healey et al., Photodeposition of micrometer-scale polymer patterns on optical imaging fibers. Science. Aug. 25, 1995; 269(5227):1078-80.
Hirschfeld, Remote and in-situ analysis. Anal Chem. 1986; 324:618-624.
Hunsaker et al., Nucleic acid hybridization assays employing dA-tailed capture probes. II. Advanced multiple capture methods. Anal Biochem. Sep. 1989; 181(2):360-70.
Johnson et al., Identification of multiple analytes using an optical sensor array and pattern recognition neural networks. Analytical Chemistry. 1997; 69(22):4641-8.
Kremsky et al., Immobilization of DNA via oligonucleotides containing an aldehyde or carboxylic acid group at the 5' terminus. Nucleic Acids Res. Apr. 10, 1987; 15(7):2891-909.
Kuang et al., Living bacterial cell array for genotoxin monitoring. Anal Chem. May 15, 2004; 76(10):2902-9.
Kuang et al., Monitoring "promiscuous" drug effects on single cells of multiple cell types. Anal Biochem. Oct. 15, 2005; 345(2):320-5.
Kuang et al., Simultaneously monitoring gene expression kinetics and genetic noise in single cells by optical well arrays. Anal Chem. Nov. 1, 2004; 76(21):6282-6.
Lafratta et al., Very high density sensing arrays. Chem Rev. Feb. 2008; 108(2):614-37. Epub Jan. 30, 2008.
Lee et al., A fiber-optic microarray biosensor using aptamers as receptors. Anal Biochem. Jun. 15, 2000; 282(1):142-6.
Li et al., Detection of single-molecule DNA hybridization using enzymatic amplification in an array of femtoliter-sized reaction vessels. J Am Chem Soc. Sep. 24, 2008; 130(38):12622-3. Epub Sep. 3, 2008.
Li et al., Molecule by molecule direct and quantitative counting of antibody-protein complexes in solution. Anal Chem. Aug. 1, 2004; 76(15):4446-51.
Lu et al., Single-molecule enzymatic dynamics. Science. Dec. 4, 1998; 282(5395):1877-82.
Luo et al., Single-molecule and ensemble fluorescence assays for a functionally important conformational change in T7 DNA polymerase. Proc Natl Acad Sci U S A. Jul. 31, 2007; 104(31):12610-5. Epub Jul. 18, 2007.
Melin et al., Microfluidic large-scale integration: the evolution of design rules for biological automation. Annu Rev Biophys Biomol Struct. 2007; 36:213-31.
Michael et al., Combined imaging and chemical sensing of fertilization-induced acid release from single sea urchin eggs. Anal Biochem. Sep. 10, 1999; 273(2):168-78.
Michael et al., Randomly ordered addressable high-density optical sensor arrays. Anal Chem. Apr. 1, 1998; 70(7):1242-8.
Monk et al., Fabrication of gold microtubes and microwires in high aspect ratio capillary arrays. J Am Chem Soc. Sep. 22, 2004; 126(37):11416-7.
Monk et al., Optical fiber-based biosensors. Anal Bioanal Chem. Aug. 2004; 379(7-8):931-45. Epub Jun. 23, 2004.
Monk et al., Progress toward the dermination of $Sr^{2+}$ in highly basic solutions using imagining optical fiber sensor arrays. J. Mater. Chem. 2005; 15:4361-4366.
Munkholm et al., Polymer modification of fiber optic chemical sensors as a method of enhancing fluroescence signal for pH measurement. Anal Chem. 1986; 58:1427-1430.
Nagai et al., High-throughput PCR in silicon based microchamber array. Biosens Bioelectron. Dec. 2001; 16(9-12):1015-9.
Nalefski et al., Single-molecule detection for femtomolar quantification of proteins in heterogeneous immunoassays. Clin Chem. Nov. 2006; 52(11):2172-5.
Nam et al., Nanoparticle-based bio-bar codes for the ultrasensitive detection of proteins. Science. Sep. 26, 2003;301(5641):1884-6.
Niemeyer et al., Combination of DNA-directed immobilization and immuno-PCR: very sensitive antigen detection by means of self-assembled DNA-protein conjugates. Nucleic Acids Res. Aug. 15, 2003; 31(16):e90, 7 pages.
Panova et al., In situ fluorescence imaging of localized corrosion with a pH-sensitive imaging fiber. Anal Chem. Apr. 15, 1997; 69(8):1635-41.

(56) References Cited

OTHER PUBLICATIONS

Pantano et al., Analytical applications of optical imaging fibers. Anal Chem. Aug. 1, 1995; 67(15):481A-487A.
Pantano et al., Ordered nanowell arrays. Chemistry of Materials. 1996;8: 2832-2835.
Pantano et al., Toward a near-field optical array. Rev. Sci. Instrum. 1997; 68(3) 1357-1359.
Peterson et al., Fiber optic pH probe for physiological use. Anal Chem. May 1980; 52(6):864-9.
Qiu et al., Fluorescence single-molecule counting assays for high-sensitivity detection of cytokines and chemokines. Clin Chem. Nov. 2007; 53(11):2010-2.
Randle et al., Integrating molecular detection and response to create self-signalling antibodies. Biochem Biophys Res Commun. Nov. 12, 2004; 324(2):504-10.
Rissin et al., Attomolar detection of proteins in serum using single molecule enzyme-linked immunosorbent assays. Quanterix Corporation. Oak Ridge Conference, San Jose, CA. Poster. 2010. 1 page.
Rissin et al., Digital concentration readout of single enzyme molecules using femtoliter arrays and Poisson statistics. Nano Lett. Mar. 2006; 6(3):520-3.
Rissin et al., Digital readout of target binding with attomole detection limits via enzyme amplification in femtoliter arrays. J Am Chem Soc. May 17, 2006; 128(19):6286-7.
Rissin et al., Distinct and long-lived activity states of single enzyme molecules. J Am Chem Soc. Apr. 16, 2008; 130(15):5349-53. Epub Mar. 5, 2008.
Rissin et al., Duplexed sandwich immunoassays on a fiber-optic microarray. Anal Chim Acta. Mar. 30, 2006; 564(1):34-9. Epub Nov. 11, 2005.
Rissin et al., Single-molecule enzyme-linked immunosorbent assay detects serum proteins at subfemtomolar concentrations. Nat Biotechnol. Jun. 2010; 28(6):595-9 and supplemental pages. Epub May 23, 2010.
Roeffaers et al., Single-molecule fluorescence spectroscopy in (bio)catalysis. Proc Natl Acad Sci USA. Jul. 31, 2007; 104(31):12603-9. Epub Jul. 30, 2007.
Rondelez et al., Highly coupled ATP synthesis by F1-ATPase single molecules. Nature. Feb. 17, 2005; 433(7027):773-7.
Rondelez et al., Microfabricated arrays of femtoliter chambers allow single molecule enzymology. Nat Biotechnol. Mar. 2005; 23(3):361-5. Epub Feb. 20, 2005.
Rotman, Measurement of activity of single molecules of beta-D-galactosidase. Proc Natl Acad Sci USA. Dec. 15, 1961; 47:1981-91.
Schauer et al., A cross-reactive, class-selective enzymatic array assay. J Am Chem Soc. Sep. 26, 2001; 123(38):9443-4.
Schmidinger, et al., Inhibitor and protein microarrays for activity-based recognition of lipolytic enzymes. Chembiochem. Mar. 2006; 7(3):527-34.
Schweitzer et al., Inaugural article: immunoassays with rolling circle DNA amplification: a versatile platform for ultrasensitive antigen detection. Proc Natl Acad Sci U S A. Aug. 29, 2000; 97(18):10113-9.
Seydack, Nanoparticle labels in immunosensing using optical detection methods. Biosens Bioelectron. Jun. 15, 2005; 20(12):2454-69. Epub Dec. 16, 2004.
Shen et al. High-throughput SNP genotyping on universal bead arrays. Mutat Res. Jun. 3, 2005;573(1-2):70-82.
Shephard et al., Array-based binary analysis for bacterial typing. Anal Chem. Jan. 1, 2005; 77(1):319-26.
Song et al., Detecting biological warfare agents. Emerg Infect Dis. Oct. 2005; 11(10):1629-32.
Song et al., Fiber-optic microsphere-based arrays for multiplexed biological warfare agent detection. Anal Chem. Feb. 15, 2006; 78(4):1023-33.
Soukka et al., Supersensitive time-resolved immunofluorometric assay of free prostate-specific antigen with nanoparticle label technology. Clin Chem. 2001; 47(7):1269-78.
Stamou et al., Self-assembled microarrays of attoliter molecular vessels. Angew Chem Int Ed Engl. Nov. 24, 2003; 42(45):5580-3.
Steemers et al., Multi-analyte sensing: from site-selective deposition to randomly ordered addressable optical sensors. Microchimica Acta. 1999; 131:99-105.
Steemers et al., Screening unlabeled DNA targets with randomly ordered fiber-optic gene arrays. Nat Biotechnol. Jan. 2000; 18(1):91-4.
Stitzel et al., Array-to-array transfer of an artificial nose classifier. Anal Chem. Nov. 1, 2001; 73(21):5266-71. Epub Sep. 28, 2001.
Subbaraman, Detecting single cancer molecules. Technol Rev. Jun. 3, 2010. Last accessed at http://www.technologyreview.com/biomedicine/25462/ on Jan. 31, 2012. 1 page.
Szunerits et al., "Aluminum Surface Corrosion and the Mechanism of Inhibitors Using pH and Metal Ion Selective Imaging Fiber Bundles," *Analytical Chemistry*, 2002, 74(4), 886-894.
Szunerits et al., "Fabrication of an Optoelectrochemical Microring Array," *Analytical Chemistry*, 2002, 74(7), 1718-1723.
Szunerits et al., Spatially resolved electrochemiluminescence on an array of electrode tips. Anal Chem. Sep. 1, 2003; 75(17):4382-8.
Szunerits et al., The use of optical fiber bundles combined with electrochemistry for chemical imaging. Chemphyschem. Feb. 17, 2003; 4(2):186-92. Epub Feb. 7, 2003.
Szurdoki et al., A duplexed microsphere-based fluorescent immunoassay. Anal Biochem. Apr. 15, 2001; 291(2):219-28.
Tam et al., An imaging fiber-based optical tweezer array for microparticle array assembly. Applied Physics Letters. 2004; 84(21):4289-4291.
Tam et al., Fabrication and optical characterization of imaging fiber-based nanoarrays. Talanta. Sep. 15, 2005; 67(3):498-502. Epub Jul. 27, 2005.
Tam et al., Parallel microparticle manipulation using an imaging fiber bundle-based optical tweezer array and a digital micromirror device. Applied Physics Letters. 2006; 89:194101/1-194101/3.
Tan et al., Monitoring the reactions of single enzyme molecules and single metal ions. Anal. Chem. 1997; 69:4242-4248.
Taylor et al., Application of high-density optical microwell arrays in a live-cell biosensing system. Anal Biochem. Feb. 15, 2000; 278(2):132-42.
Tessler et al., Protein quantification in complex mixtures by solid phase single-molecule counting. Anal Chem. Sep. 1, 2009; 81(17):7141-8.
Thaxton et al., Nanoparticle-based bio-barcode assay redefines "undetectable" PSA and biochemical recurrence after radical prostatectomy. Proc Natl Acad Sci U S A. Nov. 3, 2009;106(44):18437-42. Epub Oct. 19, 2009.
Timmerman, Quanterix CEO sets sight on early detection of cancer, neurological diseases in the blood. Xconomy. Jan. 19, 2010. Last accessed at http://www.xconomy.com/boston/2010/01/19/quanterix-ceo-sets-sight-on-early-detection-of-cancer-neurological-diseases-in-the-blood/ on Jan. 31, 2012. 4 pages.
Todd et al., Ultrasensitive flow-based immunoassays using single-molecule counting. Clin Chem. Nov. 2007; 53(11):1990-5. Epub Sep. 21, 2007.
Tromberg et al., Development of antibody-based fiber-optic sensors for detection of a benzo[a]pyrene metabolite. Anal Chem. Sep. 15, 1988; 60(18):1901-8.
Ueberfeld et al., Reversible ratiometric probe for quantitative DNA measurements. Anal Chem. Feb. 15, 2004; 76(4):947-52. Epub Jan. 20, 2004.
Vo-Dinh et al., Phase-resolved fiber-optics fluoroimmunosensor. Applied Spectroscopy. 1990; 44(1):128-132.
Walt et al., Biosensing with live cells using a high-density optical fiber array. Radiation Research. 2001; 156(4):442.
Walt et al., Microsensor arrays for saliva diagnostics. Ann N Y Acad Sci. Mar. 2007; 1098:389-400.
Walt et al., Optical sensor arrays for odor recognition. Biosens Bioelectron. Sep. 15, 1998; 13(6):697-9.
Walt et al., Ultrasensitive detection of proteins using single molecule arrays (SiMoA). Presented Mar. 1, 2010. Pittcon. Abstract and PowerPoint presentation. 32 pages.
Walt, An array of solutions, fiber arrays contribute to studies of individual cellular behavior and response. SPIE's oemagazine. 2005; 19-21.

(56) References Cited

OTHER PUBLICATIONS

Walt, Fiber optic array biosensors. Biotechniques. Nov. 2006; 41(5):529, 531, 533, 535 passim.
Walt, Fiber optic imaging sensors. Accounts of Chemical Research. 1998; 31:267-278.
Walt, Imaging optical sensor arrays. Curr Opin Chem Biol. Oct. 2002; 6(5):689-95.
Walt, Techview: molecular biology. Bead-based fiber-optic arrays. Science. Jan. 21, 2000; 287(5452):451-2.
Wang et al., Quantification of protein based on single-molecule counting by total internal reflection fluorescence microscopy with adsorption equilibrium. Anal Chim Acta. May 2, 2007; 590(1):104-9. Epub Mar. 15, 2007.
Whitaker et al., Fiber-based single cell analysis of reporter gene expression in yeast two-hybrid systems. Anal Biochem. Jan. 1, 2007; 360(1):63-74. Epub Oct. 30, 2006.
Whitaker et al., Multianalyte single-cell analysis with multiple cell lines using a fiber-optic array. Anal Chem. Dec. 1, 2007; 79(23):9045-53. Epub Nov. 1, 2007.
White et al., An olfactory neuronal network for vapor recognition in an artificial nose. Biol Cybern. Apr. 1998; 78(4):245-51.
White et al., Rapid analyte recognition in a device based on optical sensors and the olfactory system. Analytical Chemistry. 1996; 68(13):2191-2202.
Wu et al., Development and preliminary clinical validation of a high sensitivity assay for cardiac troponin using a capillary flow (single molecule) fluorescence detector. Clin Chem. Nov. 2006; 52(11):2157-9.
Xie et al., Optical studies of single molecules at room temperature. Annu Rev Phys Chem. 1998; 49:441-80.
Xie et al., Single gold nanoparticles counter: an ultrasensitive detection platform for one-step homogeneous immunoassays and DNA hybridization assays. J Am Chem Soc. Sep. 9, 2009;131(35):12763-70.
Xue et al., Differences in the chemical reactivity of individual molecules of an enzyme. Nature. Feb. 23, 1995; 373(6516):681-3.
Young et al., Integrating high-content screening and ligand-target prediction to identify mechanism of action. Nat Chem Biol. Jan. 2008; 4(1):59-68. Epub Dec. 9, 2007.
Invitation to Pay Additional Fees for PCT/US2012/022923 mailed Apr. 2, 2012.
International Preliminary Report on Patentability for PCT/US2012/022923 mailed Aug. 8, 2013.
Extended European Search Report for European Application No. 12177276.8 mailed Nov. 26, 2012.
Office Action for U.S. Appl. No. 13/527,210, filed Jun. 19, 2012, which Office Action is dated Jun. 20, 2013, and claims as pending for Office Action for U.S. Appl. No. 13/527,210 as of Jun. 20, 2013.
Notice of Allowance for U.S. Appl. No. 12/731,136, filed Mar. 24, 2010, published as 2011-0212537, which Notice of Allowance is dated Nov. 15, 2012, and claims as allowed for U.S. Appl. No. 12/731,136 as of Nov. 15, 2012.
Notice of Allowance for U.S. Appl. No. 11/707,385, filed Feb. 16, 2007, published as US-2007-0259448, which Notice of Allowance is dated Feb. 25, 2013, and claims as allowed for Office Action for U.S. Appl. No. 11/707,385 as of Feb. 25, 2013.
Notice of Allowance for U.S. Appl. No. 11/707,383, filed Feb. 16, 2007, published as US 2007-0259385, which Office Action is dated Feb. 8, 2013, and claims as allowed for U.S. Appl. No. 11/707,383 as of Feb. 8, 2013
Notice of Allowance for U.S. Appl. No. 11/707,384, filed Feb. 16, 2007, published as US 2007-0259381, which Office Action is dated Feb. 6, 2013, and claims as allowed for U.S. Appl. No. 11/707,384 as of Feb. 6, 2013.
Blicharz et al., Fiber-optic microsphere-based antibody array for the analysis of inflammatory cytokines in saliva. Anal. Chem. 2009;81(6):2106-14.
Duffy. Single Molecule Arrays (Simoa) for Ultrasensitive Protein Detection in Companion Diagnostics. Next Generation DX Summit. Aug. 22, 2012. PowerPoint presentation. 18 slides.

Kan et al., Isolation and detection of single molecules on paramagnetic beads using sequential fluid flows in microfabricated polymer array assemblies. Lab Chip. Mar. 7, 2012;12(5):977-85. Epub Dec. 16, 2011.
Rissin et al., Simultaneous detection of single molecules and singulated ensembles of molecules enables immunoassays with broad dynamic range. Anal Chem. Mar. 15, 2011;83(6):2279-85. Epub Feb. 23, 2011.
Sykes et al., Quantitation of targets for PCR by use of limiting dilution. Biotechniques. 1992;13(3):444-9.
Office Action for U.S. Appl. No. 13/527,210, filed Jun. 19, 2012, which Office Action is dated Feb. 6, 2014, and claims as pending for Office Action for U.S. Appl. No. 13/527,210 as of Nov. 20, 2013.
Notice of Allowance for U.S. Appl. No. 13/527,210, filed Jun. 19, 2012, which Notice of Allowance is dated May 27, 2014, and claims as pending for U.S. Appl. No. 13/527,210 as of Nov. 20, 2013.
Office Action for U.S. Appl. No. 13/530,979, filed Jun. 22, 2012, which Office Action is dated Jun. 19, 2015, and claims as pending for U.S. Appl. No. 13/530,979 as of Apr. 5, 2013.
Office Communication for U.S. Appl. No. 13/531,061, filed Jun. 22, 2012, which Office Communication is dated Aug. 21, 2015, and claims as pending for U.S. Appl. No. 13/531,061.
Office Communication for U.S. Appl. No. 13/035,472, filed Feb. 25, 2011, which Office Communication is dated Mar. 20, 2014, and claims as pending for U.S. Appl. No. 13/035,472.
Office Communication for U.S. Appl. No. 13/037,987, filed Mar. 1, 2011, which Office Communication is dated May 2, 2014, and claims as pending for U.S. Appl. No. 13/037,987.
Office Communication for U.S. Appl. No. 13/037,987, filed Mar. 1, 2011, which Office Communication is dated Oct. 20, 2014, and claims as pending for U.S. Appl. No. 13/037,987 as of Jul. 2, 2014.
[No Author Listed], bioMérieux and Quanterix Sign Strategic Partnership in Ultrasensitive and Multiplex Immunoassays. Quanterix Press Release. Nov. 15, 2012. 2 pages.
[No Author Listed], Does Brain Hypoxia Help Kick Off Alzheimer's Pathology? Alzheimer Research Forum. Dec. 16, 2011 http://www.alzforum.org/new/detailprint.asp?id=3002 [last accessed Jan. 30, 2012]. 4 pages.
[No Author Listed], Pittcon Announces 2010 Technical Program: Webcast of Selected Symposia. Press Release. Oct. 15, 2009. http://archive.constantcontact.com/fs033/1102032821298/archive/1102745632000.html [last accessed Jan. 31, 2012]. 2 pages.
[No Author Listed], Quanterix and STRATEC Announce Strategic Partnership. Quanterix Press Release. Aug. 16, 2011. 2 pages.
[No Author Listed], Quanterix Announces Commercial Availability of its Simoa Single Molecule Array Technology. Quanterix Press Release. Jul. 30, 2013. 2 pages.
[No Author Listed], Quanterix Digital ELISA Measures Low Abundance Biomarkers of Inflammation in Crohn's Disease. Quanterix Press Release. Aug. 19, 2011. Last accessed at http://www.quanterix.com/events-news/press-releases/item/142-quanterix-digital-elisa-measures-low-abundance-biomarkers-of-inflammation-in-crohn's-disease on Sep. 20, 2012.
[No Author Listed], Quanterix Launches Multiplexed Single Molecule Immunoassay Technology to Improve Diagnosis and Potential Treatment of Complex Diseases. Quanterix Press Release. Sep. 17, 2003. 2 pages.
[No Author Listed], Quanterix to Present Poster Session on Blood-based Brain Biomarker Measurements of Sports Related Brain Injury at Neuroscience. Quanterix Press Release. Nov. 4, 2013. 1 page.
[No Author Listed], Quanterix's Simoa technology to detect blood biomarker for concussion in hockey players. Quanterix Press Release. Mar. 14, 2014. 1 page.
[No Author Listed], Quanterix's Ultrasensitive Simoa™ Technology Forges New Ground with Direct Detection of Genomic DNA in Human Blood and River Water. Quanterix Press Release. Jan. 22, 2013. 2 pages.
[No Author Listed], Quanterix's Ultrasensitive Simoa™ Technology Demonstrates Equivalence with NAT and 3,000x Improvement in Sensitivity over Conventional Immunoassays for HIV Detection. Quanterix Press Release. Oct. 11, 2012. 1 page.

(56) References Cited

OTHER PUBLICATIONS

[No Author Listed], Scientific Principle of Simoa™ (Single Molecule Array) Technology. Whitepaper 1.0. Jul. 19, 2013. 2 pages.
Chang et al., Digital ELISA of HIV P24 capsid protein with sensitivity of nucleic acid amplification tests. 2012 AACC Meeting. Los Angeles, CA. Abstract and Poster. 2012. 2 pages.
Chang et al., Prototype digital immunoassay for troponin I with sub-femtomolar sensitivity. 2013 AACC Meeting. Houston, TX. Abstract and Poster. 2013. 2 pages.
Chang et al., Simple diffusion-constrained immunoassay for p24 protein with the sensitivity of nucleic acid amplification for detecting acute HIV infection. J Virol Methods. Mar. 2013;188(1-2):153-60. doi: 10.1016/j.jviromet.2012.08.017. Epub Oct. 2, 2012.
Chang et al., Single molecule enzyme-linked immunosorbent assays: theoretical considerations. J Immunol Methods. Apr. 30, 2012;378(1-2):102-15. doi: 10.1016/j.jim.2012.02.011. Epub Apr. 30, 2013. 28 pages.
Duffy et al., Detection of prostate specific antigen (PSA) in the serum of radical prostatectomy patients at femtogram per milliliter levels using digital ELISA (AccuPSATM) based on single molecule arrays (SiMoA). AACC Meeting Poster. 2010. 1 page.
Duffy, Immunoassays with Broad Dynamic Ranges based on Combining Digital and Digitally Enhanced Analog Detecion of Enzyme Labels. Oak Ridge Conference. Presentation. Apr. 15, 2011. 16 pages.
Duffy, Ultra-sensitive protein detection using single molecule arrays (Simoa): the potential for.detecting single molecules of botulinum toxin. The Botulinum J. 2012;2(2):164-7.
Joos, Quanterix Web Symposium: Immunoassays in Multiplex for Biomarker Discovery and Validation. Presentation. Feb. 27, 2013. 43 pages.
Okrongly, Single Molecule Enzyme Detection and Application to Immunoassay: Implications for Personalized Medicine. Abstract and Presentation. ISE International Conference. May 4, 2010. 24 pages.
Prabhakar et al., Simultaneous quantification of proinflammatory cytokines in human plasma using the LabMAP assay. J Immunol Methods. Feb. 1, 2002;260(1-2):207-18.
Rissin et al., Immunoassays with broad dynamic ranges based on combining digital and digitally-enhanced analog detection of enzyme labels. Oak Ridge Conference. Poster 7 and Abstract. Apr. 14-15, 2011. 2 pages.
Rissin et al., Multiplexed single molecule immunoassays. Lab Chip. Aug. 7, 2013;13(15):2902-11. doi: 10.1039/c31c50416f.
Song et al., Direct Detection of Bacterial DNA and viral RNA at Subfemtomolar Concentrations Using Single Molecule Arrays (Simoa). 2013 Oakridge Conference. Baltimore, MD. Abstract and Poster. 2013. 2 pages.
Song et al., Direct detection of bacterial genomic DNA at sub-femtomolar concentrations using single molecule arrays. Anal Chem. Feb. 5, 2013;85(3):1932-9. doi: 10.1021/ac303426b. Epub Jan. 18, 2013.
Song et al., Single molecule measurements of tumor necrosis factor α andinterleukin-6 in the plasma of patients with Crohn's disease. J Immunol Methods Sep. 30, 2011;372(1-2):177-86. Epub Jul. 27, 2011.
Tanen et al., Development of an Ultrasensitive Digital Immunoassay on the Single Molecule Array (SimoaTM) Platform. 2014 AAPS Annual Meeting. San Diego, CA. Abstract and Poster. Nov. 2-6, 2014. 2 pages.
Walt, Optical methods for single molecule detection and analysis. Anal Chem. Feb. 5, 2013;85(3):1258-63. doi: 10.1021/ac3027178. Epub Dec. 19, 2012.
Wilson et al., Development of AccuPSA™, a novel digital immunoassay for sub-femtomolar measurement of PSA in post radical prostatectomy patients. AACR Molecular diagnostics in Cancer Therapeutic Development Poster. 2011. 1 page.
Wilson et al., Fifth-generation digital immunoassay for prostate-specific antigen by single molecule array technology. Clin Chem. Dec. 2011;57(12):1712-21. Epub Oct. 13, 2011.
Wilson et al., Simoa™ HD-1: a fully automated digital immunoassay analyzer capable of single molecule counting, sub-femtomolar sensitivity, and multiplexing. 2014 AACC Meeting. Chicago, IL. Abstract and Poster. 2014. 2 pages.
Wilson, Serum Measurement of Hypoxia-Induced Amyloid Beta 1-42 Following Resuscitation from Cardiac Arrest. Abstract and Poster. American Academy of Neurology Annual Meeting. Apr. 9, 2011. 2 pages.
Yan et al., Analyzing polyubiquitin chains upon ubiquitin activating enzyme inhibition from cell culture & tumor lysates using the Quanterix's single molecule array (Simoa) technology. 2013 Society for the Laboratory Automation & Screening Annual Meeting. Orlando, FL. Abstract and Poster. 2013. 2 pages.
U.S. Appl. No. 11/707,383, filed Feb. 16, 2007, Walt et al.
U.S. Appl. No. 11/707,384, filed Feb. 16, 2007, Walt et al.
U.S. Appl. No. 11/707,385, filed Feb. 16, 2007, Walt et al.
U.S. Appl. No. 12/236,486, filed Sep. 23, 2008, Duffy et al.
U.S. Appl. No. 12/731,130, filed Mar. 24, 2010, Duffy et al.
U.S. Appl. No. 12/731,136, filed Mar. 24, 2010, Rissin et al.
U.S. Appl. No. 13/527,210, filed Jun. 19, 2012, Duffy et al.
U.S. Appl. No. 13/530,979, filed Jun. 22, 2012, Duffy et al.
U.S. Appl. No. 13/531,061, filed Jun. 22, 2012, Duffy et al.
U.S. Appl. No. 13/768,843, filed Feb. 15, 2013, Rissin et al.
U.S. Appl. No. 13/035,472, filed Feb. 25, 2011, Fournier et al.
U.S. Appl. No. 13/037,987, filed Mar. 1, 2011, Rissin et al.
U.S. Appl. No. 12/675,686, filed Apr. 4, 2011, Walt et al.
U.S. Appl. No. 13/870,596, filed Apr. 25, 2013, Walt et al.

* cited by examiner

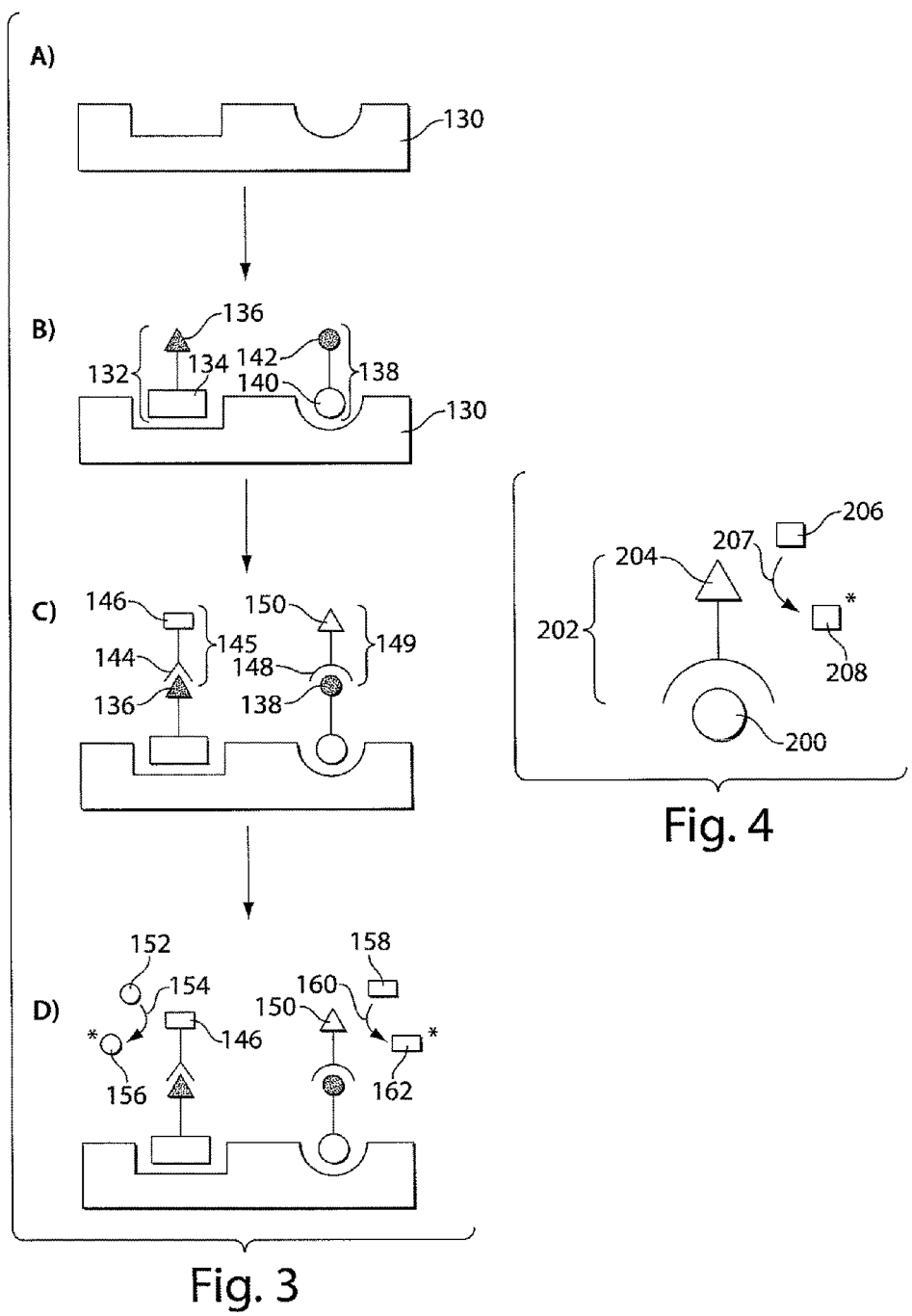

ULTRA-SENSITIVE DETECTION OF MOLECULES USING DUAL DETECTION METHODS

RELATED APPLICATIONS

This application claims the benefit of U.S. Provisional Patent Application Ser. No. 61/309,170, filed Mar. 1, 2010, entitled "Ultra-Sensitive Detection of Molecules Using Dual Detection Methods," by Duffy et al., herein incorporated by reference.

FIELD OF THE INVENTION

Described herein are systems and methods for the detection and/or determination of a measure of the concentration of analyte molecules or particles in a fluid sample. In some cases, the systems and methods employ techniques to reduce or limit negative effects associated with non-specific binding.

BACKGROUND OF THE INVENTION

Methods and systems that are able to quickly and accurately detect and, in certain cases, quantify a target analyte molecule in a sample are the cornerstones of modern analytical measurements. Such systems and methods are employed in many areas such as academic and industrial research, environmental assessment, food safety, medical diagnosis, and detection of chemical, biological, and/or radiological warfare agents. Advantageous features of such techniques may include specificity, speed, and sensitivity.

Many of the known methods and techniques are plagued with problems of non-specific binding, which is the binding of analyte molecules or particles to be detected or reporter species non-specifically to sites other than those expected. Non-specific binding events can lead to an increase in the background signal, and can affect the accuracy of the concentration determination and/or limit the lowest concentration that may be accurately or reproducibly detected.

Accordingly, improved methods for reducing the effects of non-specific binding events are needed, especially in samples where such molecules or particles are present at very low concentration.

SUMMARY OF THE INVENTION

Described herein are systems and methods for the detection and/or determination of a measure of the concentration of analyte molecules or particles in a fluid sample, and in some cases, the systems and methods employ techniques to reduce or limit the negative effects associated with non-specific binding events. The subject matter of the present invention involves, in some cases, interrelated products, alternative solutions to a particular problem, and/or a plurality of different uses of one or more systems and/or articles.

In some embodiments, a method for determining a measure of the concentration of analyte molecules or particles in a fluid sample comprises providing the analyte molecules or particles immobilized with respect to a binding surface having affinity for at least one type of analyte molecule or particle, the binding surface forming or contained within one of a plurality of locations on a substrate, such that at least some of the plurality of locations contain at least one analyte molecule or particle and a statistically significant fraction of the plurality of locations do not contain any analyte molecules or particles, exposing the analyte molecules or particles to a first type of binding ligand having an affinity for a first epitope on the analyte molecules or particles and a second type of binding ligand having an affinity for a second epitope on the analyte molecules or particles, addressing at least a portion of the plurality of the locations and determining the number of said locations containing a first type of binding ligand and a second type of binding ligand, and determining a measure of the concentration of analyte molecules or particles in the fluid sample based at least in part on the number of locations containing both a first type of binding ligand and a second type of binding ligand.

In some embodiments, a method for determining a measure of the concentration of analyte molecules or particles in a fluid sample comprises providing a fluid sample containing or suspected of containing a plurality of analyte molecules or particles, exposing the plurality of analyte molecules or particles to a first type of binding ligand having an affinity for a first epitope on the analyte molecules or particles and a second type of binding ligand having an affinity for a second epitope on the analyte molecules or particles, spatially separating at least a portion of the analyte molecules or particles into a plurality of locations, such that at least some of the plurality of locations contain at least one analyte molecule or particle and a statistically significant fraction of the plurality of locations do not contain any analyte molecules or particles, addressing at least a portion of the plurality of locations and determining the number of said locations containing both a first type binding ligand and a second type of binding ligand, and determining a measure of the concentration of analyte molecules or particles in the fluid sample based at least in part on the number of locations containing both a first type of binding ligand and a second type of binding ligand.

BRIEF DESCRIPTION OF THE DRAWINGS

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents mentioned in the text are incorporated by reference in their entirety. In case of conflict between the description contained in the present specification and a document incorporated by reference, the present specification, including definitions, will control.

FIG. 3 is a schematic flow diagram depicting one embodiment of steps (A-D) for performing an exemplary method of the present invention;

FIG. 4 illustrates an exemplary method of indirect detection;

DETAILED DESCRIPTION

Figure 1:
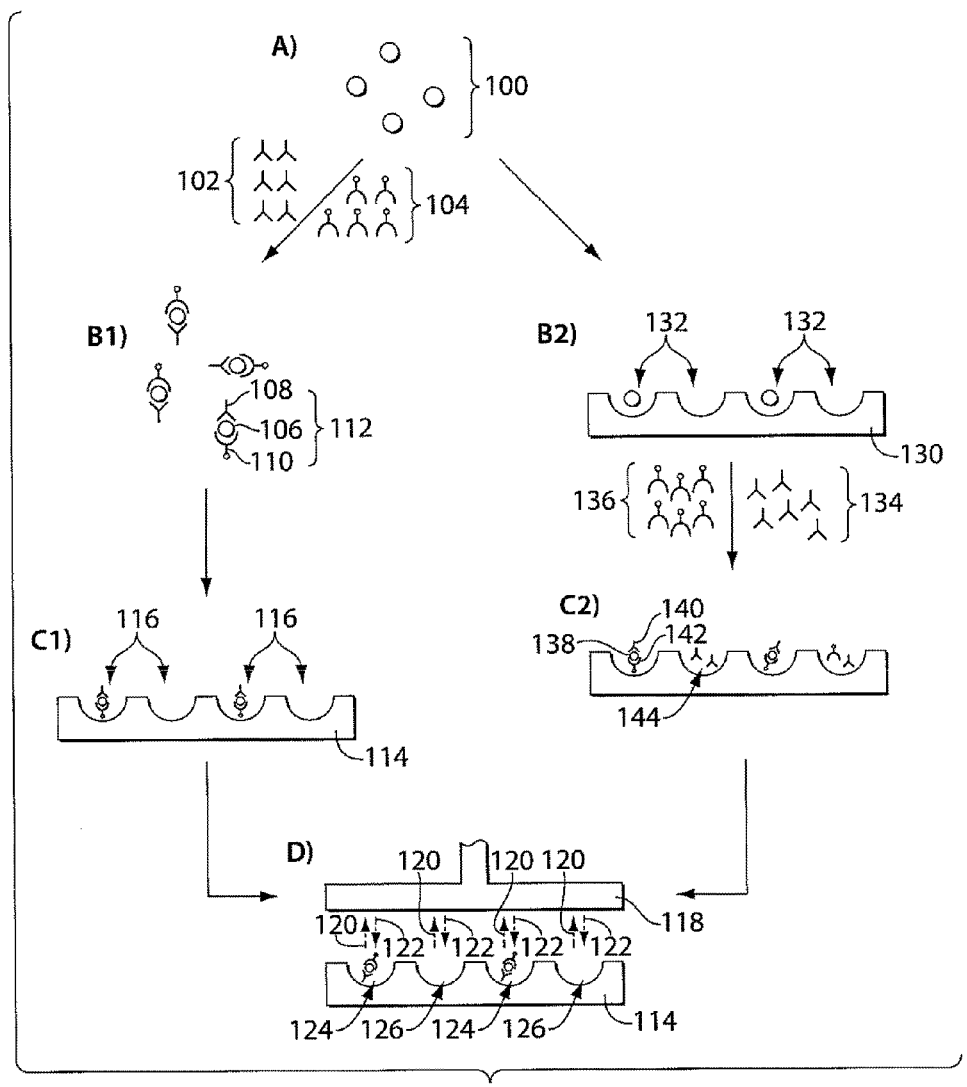
FIG. 1 is a schematic flow diagram depicting embodiments of steps (A-B1-C1-D) and (A-B2-C2-D) for performing exemplary methods of the present invention.

Described herein are systems and methods for the detection and/or determination of a measure of the concentration of analyte molecules or particles (such as, for example, cells, cell organelles and other biological or non-biological particulates) in a fluid sample that, in some cases, employ techniques to reduce or limit negative effects associated with non-specific binding events. The subject matter of the present invention involves, in some cases, interrelated products, alternative solutions to a particular problem, and/or a plurality of different uses of one or more systems and/or articles. It should be understood, that while much of the discussion below is directed to analyte molecules, this is by way of example only, and other materials may be detected and/or quantified, for example, analytes in particulate form. Some exemplary analyte molecules and particles are described herein.

The systems and methods of the present invention, in certain instances, may help reduce or limit certain negative effects of non-specific binding events on detection sensitivity and/or accuracy when compared to typical conventional systems and methods for performing similar assays. Non-specific binding is the binding or association in a non-specific fashion of one component of an assay with another component of the assay with which it is not desirable that it interact. For example, association, binding, or immobilization of a binding ligand with a substrate or assay material as opposed to with an analyte molecule or particle to which it has binding specificity. Non-specific binding may lead to false positive signals and may not only affect the accuracy of the assay measurement, but may also limit the lowest level of detection. Therefore, certain methods and/or systems of the present invention that provide improvements in reducing the negative effects of non-specific binding may allow for the detection and/or quantification of analyte molecules in a sample at a lower detection limit and/or with greater accuracy as compared to typical conventional technologies. In addition, certain embodiments of the methods and/or systems of the present invention may also allow for the detection and/or quantification of analyte molecules in certain samples in which such analyte molecules have previously been undetected and/or unquantifiable because of the very low concentration at which they are present.

In some embodiments, the methods of the present invention may be used in conjunction with methods or systems used for determining a measure of the concentration of analyte molecules in a fluid sample. In some cases, the methods and systems may comprise the detection and/or quantification of single analyte molecules. In certain such embodiments, the analyte molecules in the fluid sample may be spatially segregated into a plurality of locations (e.g., on a surface) such that each analyte molecule can be individually interrogated. In some cases, the methods and systems involve immobilizing the plurality of analyte molecules with respect to a plurality of locations, wherein at least some, and in certain embodiments substantially each, location comprises either zero or one analyte molecules. A measure of the concentration of analyte molecules in the fluid sample may be determined using a binary read-out system, wherein the measure of the concentration is determined at least in part based on the number of locations which are determined to contain an analyte molecule. That is, a binary read-out method comprises determining a measure of the concentration of analyte molecules in a fluid sample at least in part on the number of "on" locations (e.g., locations with a positive signal). For examples of non-limiting methods and systems, see U.S. patent application Ser. No. 12/731,130, entitled "Ultra-Sensitive Detection of Molecules or Particles using Beads or Other Capture Objects," by Duffy et al., filed Mar. 24, 2010; U.S. Patent Application No. 20070259448, entitled "Methods and arrays for target analyte detection and determination of target analyte concentration in solution," by Walt et al., filed Feb. 16, 2007; U.S. Patent Application No. 20070259385, entitled "Methods and arrays for detecting cells and cellular components in small defined volumes," by Walt et al., filed Feb. 16, 2007; U.S. Patent Application No. 20070259381, entitled "Methods and arrays for target analyte detection and determination of reaction components that affect a reaction," by Walt et al., filed Feb. 16, 2007; International Patent Application No. PCT/US07/019184, entitled "Methods for Determining The Concentration of an Analyte In Solution," by Walt et al., filed Aug. 20, 2007; International Patent Application No. PCT/US09/005428, entitled "Ultra-Sensitive Detection of Molecules or Enzymes," by Duffy et al., filed Sep. 9, 2009; and U.S. patent application Ser. No. 12/731,136, filed Mar. 24, 2010, entitled "Methods and systems for extending dynamic range in assays for the detection of molecules or particles," by Rissin, et al., herein incorporated by reference.

The methods of the present invention may reduce certain negative effects of non-specific binding by employing detection methods which involve the association of at least two components (e.g., binding ligands) with each analyte molecule for detection of the analyte molecule. Certain such methods can reduce the number of false positive (e.g., non-specific events) as compared to methods which require only a single component for detection. This can be easily understood when comparing two methods which either employ one component or two components for detection. For methods which require only a single component to associate with an analyte molecule for detection, generally, a significant number of these single components may bind non-specifically to locations. Each instance of non-specific binding of a single component with a location results in the determination of an "on" location (e.g., a false positive), thus increasing the effective number locations determined to contain an analyte molecule, and thereby directly affecting a parameter (i.e., the number of "on" locations) used to calculate a measure of the concentration of analyte molecules in the fluid sample when using a binary read-out digital detection mode of quantification. In a two component system, only locations which contain both components are determined to be "on" locations. The probability of both components binding non-specifically in a single location, which would result in a false positive, may be significantly smaller as compared to the number of false positives that would be observed for a single component system, when assuming that the non-specific binding affinity for the types of components are the same. Thus a two component system can result in a decrease in the number of false positives caused by non-specific binding of a binding ligand, thereby effectively reducing effects of non-specific binding events on the concentration determination.

For example, in one embodiment, a plurality of analyte molecules is spatially separated into a plurality of locations. Two types of components are provided to the assay under conditions such that substantially all analyte molecules associate with (e.g., specifically bind to) at least one of each type of component. The analyte molecules are then individually interrogated. Only locations which contain at least one of each type of component are determined to be a location which comprises an analyte molecule. Locations that only contain a single component are considered to be locations which do not contain an analyte molecule (e.g., location in which a single component has non-specifically bound are treated as "off" locations), and do not affect the determination of the measure of the concentration of analyte molecules in a fluid sample. As a comparison, consider a method conducted using the same steps as outline above, but with only a single component being used to facilitate detection. In such a method, locations which contain a single component due to non-specific binding are indistinguishable from locations which contain an analyte molecule and a single component. Thus, locations with only a single binding ligand are considered to be "on" locations (e.g., location in which a single component has non-specifically bound resulting in a false positive signal) and would undesirably affect the determination of the measure of the concentration of analyte molecules in a fluid sample.

In some embodiments, the methods of the present invention comprise the use of a plurality of types of binding ligands (examples of components for detection). A "binding ligand," as used herein, is any molecule, particle, or the like, which specifically binds to or otherwise specifically associates with an analyte molecule or another binding ligand and may aid in the detection of the analyte molecule. In some cases, at least two, at least three, at least four, at least five, at least six, at least seven, at least eight, at least nine, at least ten, or more, binding ligands may be employed. A plurality of analyte molecules may be exposed to the differing types of binding ligands substantially simultaneously and/or substantially sequentially.

Binding ligands may aid in the detection of analyte molecules. For example, certain binding ligands comprise an entity which is able to facilitate detection, either directly (e.g., via a detectable moiety) or indirectly. In the case of direct detection, the binding ligands may comprise a molecule or moiety that may be directly interrogated and/or detected (e.g., a fluorescent entity). In the case of indirect detection, an additional component is used for determining the presence of the binding ligand. For example, a binding ligand associated with an analyte molecule may be exposed to a precursor labeling agent, wherein the precursor labeling agent is converted into a labeling agent upon exposure to the binding ligand associated with an analyte molecule, and the labeling agent is directly detected. As another example, a component (e.g., a third type of binding ligand) may be provided which associates with a first type of binding ligand and a second type of binding ligand which are both immobilized with respect to an analyte molecule. The third type of binding ligand may be detected (e.g., directly or indirectly). The binding ligands which are to be detected may comprise or create a measurable entity or parameter (e.g., fluorescence) which makes it distinguishable from all other types of binding ligands employed in an assay which are to be detected, thus allowing for the determination of which binding ligands are present at/in a location.

Binding ligands may be selected to interact with other assay components (e.g., analyte molecules, other types of binding ligands, precursor labeling agents, etc.), in a variety of ways, as is described in more detail below. In certain embodiments, at least one type of binding ligand in the assay is selected such that it becomes immobilized with respect to an analyte molecule. In some embodiments, at least two types of binding ligands become immobilized with respect to an analyte molecule. The at least two types of binding ligands may either associate with the same or different components or moieties (e.g., epitopes) of an analyte molecule.

As an exemplary method employing two types of binding ligands, the method may first comprise exposing a plurality of analyte molecules to a plurality of a first type of binding ligand and plurality of a second type of binding ligand. The conditions may be selected such that substantially all of the analyte molecules are immobilized with respect to at least one of the first type of binding ligand and at least one of the second type of binding ligand. The analyte molecules (immobilized with respect to a plurality of binding ligands) are then spatially segregated into a plurality of locations on a surface, and in some cases, are spatially segregated such that each location contains zero or one analyte molecules. Alternatively, the analyte molecules may first be spatially segregated into a plurality of locations such that each location contains zero or one analyte molecules prior to being exposed to a plurality of a first type of binding ligand and a second type of binding ligand such that substantially all of the analyte molecules associate with at least a first type of binding ligand and at least a second type of binding ligand. At least a portion of the locations (e.g., comprising zero or one analyte molecules, the analyte molecules associates with at least one of a first type of binding ligand and at least one of a second type of binding ligand) may be interrogated/analyzed to determine the number of locations which contain both a first type of binding ligand and a second type of binding ligand (e.g., either by direct or indirect detection, as described herein). The first type of binding ligand may possess, create or be made to create a first measurable parameter and the second type of binding ligand may possess, create or be made to create a second measurable parameter, wherein the first measurable parameter is distinguishable from the second measurable parameter. The number of locations which contain both binding ligands can be related to the number of locations which contain an analyte molecule. A measure of the concentration of analyte molecules in the fluid sample may be based at least in part on the number of locations which contain both a first type and a second type of binding ligand. Locations which contain only a first type of binding ligand or only a second type of binding ligand would be indicative of locations in which non-specific binding of a binding ligand had occurred, and therefore, these locations would not be considered in determining the total number of locations which comprise an analyte molecule. The first type of binding ligand and the second type of binding ligand may associate with the same or different epitopes of an analyte molecule.

Exemplary embodiments of inventive assay methods involving two types of binding ligands are illustrated in FIG. 1. A plurality of analyte molecules 100 are provided, as illustrated in step (A). In a first method, plurality of analyte molecules 100 are exposed to plurality of a first type of binding ligand 102 and plurality of second type of binding ligand 104. The conditions are selected such that substantially each of the analyte molecules associate with a first type of binding ligand and a second type of binding ligand. For example, as illustrated in step (B1), analyte molecule 106 is associated with one of a first type of binding ligand 108 and one of a second type of binding ligand 110, to form complex 112. The plurality of analyte molecules from step (B1) may then be spatially segregated into a plurality of locations. As shown in step (C1), the plurality of locations is illustrated as substrate 114 comprising a surface containing a plurality of wells/reaction vessels 116. In this example, each reaction vessel comprises either zero or one analyte molecules. At least some of the reaction vessels may then be addressed (e.g., optically or via other detection means) to determine the number of locations containing an analyte molecule by determining the number of locations which contain a first type of binding ligand and a second type of binding ligand. For example, as shown in step (D), the plurality of reaction vessels are interrogated optically using light source 118, wherein each reaction vessel is exposed to electromagnetic radiation (represented by arrows 122) from light source 118. The light emitted (represented by arrows 120) from each reaction vessel is detected (and/or recorded) by detector 118 (in this example, housed in the same system as light source 118). The number of reaction vessels containing a first type of binding ligand and a second type of binding ligand (e.g., reaction vessels 124), and hence an analyte molecule, are determined, for example, based on the light emitted from the reaction vessels. In some cases, the number of reaction vessels which do not contain both a first type of binding ligand and a second type of binding ligand (e.g., reaction vessels 126), and/or the total number of wells addressed may also be determined. In some cases, at least one wash step may be performed (e.g., to remove any unbound binding ligands (e.g., prior to or following step (C1)).

Alternatively, following providing a plurality of analyte molecules as shown in step (A), the analyte molecules may be first spatially segregated into a plurality of locations, as shown in step (B2). The plurality of locations is illustrated as substrate 130 comprising a surface containing a plurality of wells/reaction vessels 132. In this example, each reaction vessel comprises either zero or one analyte molecules. The plurality of locations may be exposed to plurality of a first type of binding ligand 134 and plurality of a second type of binding ligand 136 under conditions such that substantially all of the analyte molecules associate with a first type of binding ligand and a second type of binding ligand. For example, as shown in step (C2), analyte molecule 138 is associated with first type of binding ligand 140 and second type of binding ligand 142. The reaction vessels which do not contain an analyte molecule may contain at least one binding ligand (e.g., reaction vessels 144). Following step (C2), in some embodiments, at least one wash step may be performed to aid in the removal of the binding ligand from the reaction vessels which do not contain an analyte molecule (e.g., reaction vessels 144 in step (C2)). Additionally, in some cases, the analyte molecules may be contained and/or immobilized in the reaction vessels such that the wash step does not cause the analyte molecules to be washed from the reaction vessels (e.g., via immobilization of the analyte molecule with respect to a surface of the reaction vessels, via aid of a surface comprising or contained in (e.g., on a capture object such as a bead) that has affinity for the analyte molecule). Following step (C2) and/or at least one wash step, at least some of the reaction vessels may then be addressed (e.g., optically or via other excitation/detection means) to determine the number of locations containing an analyte molecule by determining the number of locations which contain a first type of binding ligand and a second type of binding ligand. This may be carried out in a manner similar to that described above for FIG. 1, step (D).

Figure 7:
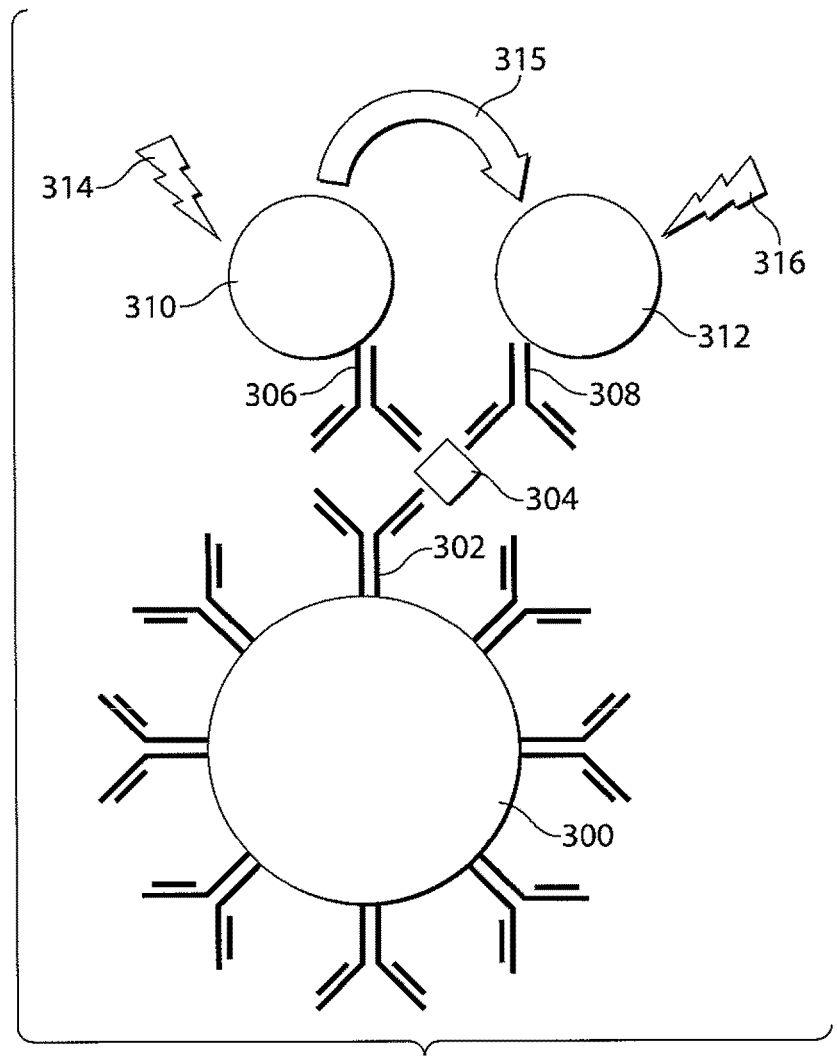
FIG. 7 illustrates an exemplary method of indirect detection.

In some embodiments, the first type of binding ligand and the second type of binding ligand may each comprise a component which work in synergy, and the detection of both types of binding ligands may occur only in cases where the first type of binding ligand and the second type of binding ligand are within close proximity of each other (e.g., immobilized with respect to the same analyte molecule). For example, the first type of binding ligand may comprise a component which upon stimulation, releases an excitation moiety. The excitation moiety may interact with a component on the second type of binding ligand. Provided the second type of binding ligand is within close proximity to the first type of binding ligand, the excitation moiety may interact with the component on the second type of binding ligand, allowing for the detection of the both the first and the second type of binding ligand. For example, as shown in FIG. 7, bead 300 contains a plurality of capture components 302. Analyte molecule 304 is associated with bead 300. First type of binding ligand 306 comprising first component 310 and second type of binding ligand 308 comprising second component 312 are both associated with analyte molecule 304. First component 310 is stimulated, in this example, with electromagnetic radiation 314. Upon stimulation, first component 310 releases an excitation moiety which excites second component 312, as indicated by arrow 315. Second component releases energy 316 upon interaction with the excitation moiety, the energy 316 being detected. As a specific embodiment, the first component may release a singlet oxygen donor that can diffuse about 200 nm before become quenched. Thus, if the second component associated with the second type of binding ligand is within 200 nm and the second component comprises a dye that is sensitive to singlet oxygen, the second component can be induced to release a signal which is detectable (e.g., fluorescence). For a non-limiting example of potentially compatible proximity sensitive detection facilitating components see Clinical Chemistry, 42 (9), 1996, 1518-1526.

As another example, both the first type of binding ligand and the second type of binding ligand may comprise an enzymatic component as a precursor labeling agent/labeling agent, and the labeling agent produced from the conversion of a first type of precursor labeling agent may act as the precursor labeling agent for the enzymatic component on the second type of binding ligand converting it to the detected labeling agent. A "precursor labeling agent" is any molecule, particle, or the like, that can be converted to a labeling agent upon exposure to a suitable converting agent (e.g., an enzymatic component). A "labeling agent" is any molecule, particle, or the like, that facilitates detection, by acting as the detected entity, using a chosen detection technique. In one non-limiting example, the product of one enzymatic conversion may be the substrate for a second enzymatic component (e.g., a coupled enzyme system). As a specific example, the coupled assay for the enzyme hexokinase (enzymatic component comprised in first type of binding ligand), which can be detected by coupling its production of glucose-6-phosphate to NADPH production, using glucose-6-phosphate dehydrogenase (enzymatic component comprised in second type of binding ligand). The NADPH may be detected to determine the presence of both the first type of binding ligand and the second type of binding ligand in a reaction vessel.

In some cases, both the first type of binding ligand and the second type of binding ligand comprise enzymatic components, and the labeling agent produced in one conversion reaction optically couples with the labeling agent produced in the second conversion reaction. For example, the product of one enzyme reaction optically couples to the detection of the second, e.g., the two enzymes produce a FRET pair where the fluorescence emission from product (e.g., donor) one excites fluorescence in the second product (e.g., acceptor). The fluorescence from the second product is detected to determine the presence of both the first type of binding ligand and the second type of binding ligand in a reaction vessel. Non-limiting examples of such donor/acceptor products include fluorescein/tetramethylrhodamine, IAEDANS/fluorescein, EDANS/dabcyl; fluorescein/fluorescein; BODIPY FL/BODIPY FL; fluorescein/QSY 7 and QSY 9, and the like.

In some cases, both the first type of binding ligand and the second type of binding ligand may be DNA labeled. When both types of binding ligands are in close proximity (e.g., associated with an analyte molecule), a connecting piece of DNA may be provided which is able to bridge the two DNA labels. A ligase can then be provided which connects the two DNA labels. Once connected, the contiguous piece of DNA can be replicated into many copies using PCR. Real time PCR in the reaction vessels may be used to detect the presence of both the first type of binding ligand and the second type of binding ligand in the reaction vessel. For non-limiting examples of DNA labels which may potentially be useful for the above detection scheme, see Nature Methods, 4 (4), 2007, 327-329, and Nature Methods, 4 (2), 2007, 135-137.

In some cases, the first type of binding ligand may comprise a first portion of an enzyme and the second type of binding ligand may comprise a second portion of an enzyme. When the binding ligands are in close proximity to each other (e.g., two binding ligands are associated with a single analyte molecule), the two enzyme portions may interact with each other. When the two binding ligands are close together, the full enzyme structure may form and be detected (e.g., via exposure to a precursor labeling agent). For non-limiting examples of enzymes which may be partitioned and used in the present invention as described above, see Biochemical and Biophysical Research Communications 370, 2008, 164-168, and Journal of Immunological Methods, 279, 2003, 209-218.

In some embodiments, more than two types of binding ligands may be employed. In some cases, three types of binding ligands may be employed. In some cases, the third type of binding ligand may function in a similar manner as the first type of binding ligand and the second type of binding ligand as described in the assays illustrated in FIG. 1. That is, the third type of binding ligand may associate with a component (e.g., an epitope) of the analyte molecule, and the presence of the first, second, and third types of binding ligands at a location may be used as an indicator of the presence of an analyte molecule at/in that location. The epitope of the analyte molecule with which the third binding ligand associates may be the same and/or different than the epitopes the first type of binding ligand and the second type of binding ligand associate with.

In other cases, the third type of binding ligand may function in a different manner as compared to the first type of binding ligand and the second type of binding ligand as described herein. For example, the first type of binding ligand and the second type of binding ligand may associate with an analyte molecule (e.g., as described in the assay method illustrated in FIG. 1) and the third type of binding ligand may associate with the first type of binding ligand and the second type of binding ligand. For the third type of binding ligand to associate with both the first type of binding ligand and the second type of binding ligand, the first and second types of binding ligands may be required to be in substantially close proximity to each other (e.g., via association with the same analyte molecule), therefore facilitating detection of the analyte molecule (e.g., by association and detection of the third type of binding ligand). The number of locations which contain the third type of binding ligand can be related to the number of locations containing both a first type of binding ligand and a second type of binding ligand in close proximity, and hence, the number of analyte molecules. In some cases, the first type of binding ligand and the second type of binding ligand may each incorporate a component (e.g., such as a DNA label) and a third type of binding ligand may comprise two complimentary components to the components of the first type and second type of binding ligand (e.g., two types of complimentary DNA labels).

Figure 2:
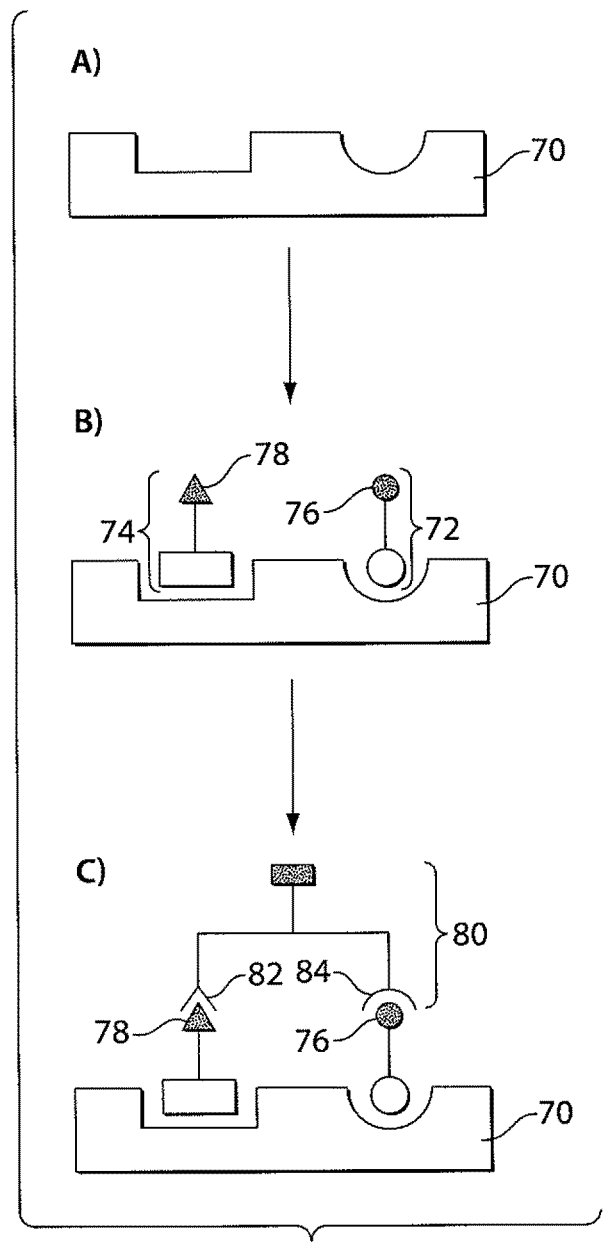
FIG. 2 is a schematic flow diagram depicting one embodiment of steps (A-C) for performing an exemplary method of the present invention.

An exemplary embodiment of steps of an inventive assay method involving three types of binding ligands is illustrated in FIG. 2. An analyte molecule 70 (illustrated schematically as comprising two distinct epitopes) is provided, as shown in step (A). For the sole purpose of simplifying this illustrative example, only a single analyte molecule is illustrated, however generally a plurality of analyte molecules is provided. Analyte molecule 70 is exposed to a first type of binding ligand 74 and a second type of binding ligand 72 under conditions such that analyte molecule 70 associates with both types of binding ligand, as shown in step (B). First type of binding ligand 74 comprises component 78 for association with a third type of binding ligand and second type of binding ligand 72 comprises component 76 for association with a third type of binding ligand. In this embodiment, neither the first type of binding ligand nor the second type of binding ligand is directly detected in the assay. In step (C), the complex from step (B) is exposed to third type of binding ligand 80 under conditions such that third type of binding ligand 80 associates with first type of binding ligand 74 and second type of binding ligand 72. Third binding ligand comprises components 82 and 84 for association with and affinity for component 78 of first type of binding ligand 74 and association with and affinity for component 76 of second type of binding ligand 72, respectively. The presence of an analyte molecule at/in a location may be detected by detecting the third type of binding ligand at the location.

Those of ordinary skill in the art will be able to use this exemplary embodiment of the use of three types of binding ligands with various other steps of assay methods described herein. For example, as describe in relation to FIG. 1, the analyte molecules may be spatially segregated into a plurality of locations prior to and/or after exposure to the types of binding ligands. The different types binding ligands may be provided substantially simultaneously and/or sequentially. Additionally, at least one wash step may be performed. The third binding ligand may be detected directly or indirectly. For example, a fourth type, etc. of binding ligand may be provided, wherein the fourth type of binding ligand associates with the third type of binding ligand. The fourth type of binding ligand may be detected directly (e.g., a fluorescent entity) or indirectly (e.g., using a precursor labeling agent which is converted to a labeling agent upon exposure to the fourth type of binding ligand).

An exemplary embodiment of steps of an inventive assay method involving four types of binding ligands is illustrated in FIG. 3. Analyte molecule 130 is provided, as shown in step (A). Analyte molecule 130 is exposed to first type of binding ligand 132 and second type of binding ligand 138 such that analyte molecule 130 associates with at least one of each type, as shown in step (B). First type of binding ligand 132 comprises component 134 for associating with analyte molecule 130 and component 136 for associating with a third type of binding ligand. Second type of binding ligand 138 comprises component 140 for associating with analyte molecule 130 and component 142 for associating with a fourth type of binding ligand. In step (C), the analyte molecule from step (B) is exposed to third type of analyte molecule 145 and fourth type of binding ligand 149. Third type of binding ligand comprises component 144 for associating with component 136 of first type of binding ligand and component 146 for detection. Fourth type of binding ligand comprises component 148 for associating with component 138 of second type of binding ligand and component 150 for detection. In some cases, components 146 and 150 are distinguishable from each other and may be detected directly (e.g., a fluorescent entity). Following spatial segregation into a plurality of locations, locations which are determined to contain third type of binding ligand 145 and fourth type of binding ligand 149 (e.g., via detection of components 146 and 150), can be related to the number of locations which contain a first type and a second type of binding ligand, respectively, and hence, an analyte molecule.

In other cases, as shown in step (D), components 146 and 150 may be detected indirectly via exposure to first type of precursor labeling agent 152 and second type of precursor labeling agent 158, wherein first type of precursor labeling agent 152 is converted to labeling agent 156 upon exposure to component 146, as indicated by arrow 154 and second type of precursor labeling agent 158 is converted to labeling agent 162 upon exposure to component 150 as indicated by arrow 160, and wherein first type of labeling agent 156 is distinguishable from second type of labeling agent 162. Following spatial segregation of the analyte molecules into a plurality of locations, locations which are determined to contain first type of labeling agent 156 and second type of labeling agent 162 are determined to contain a third and fourth type of binding ligand, thus a first and second type of binding ligand, and hence an analyte molecule.

Non-limiting examples of first type of binding ligand components for associating with a third type of binding ligand (e.g., component 136 of first binding ligand in FIG. 3; or component 138 or second binding ligand) and third type of binding ligand components for associating with the component from the first type of binding ligand (e.g., component of third binding ligand in FIG. 3; or component 148 of fourth binding ligand) are biotin/streptavidin, biotin/anti-biotin, fluorescein/anti-fluorescein, digoxin/anti-digoxin. and dinitrophenol (DNP)/anti-DNP. The third binding ligand may further comprise an enzymatic component (e.g., component 146 of third binding ligand in FIG. 3), as described herein.

Those of ordinary skill in the art will be able to determine, based on the teachings of this specification, numerous other combinations of types of binding ligands and detection methods to carry-out an assay of the present invention. For example, in the case of an assay method involving two types of binding ligands, the first type of binding ligand may comprise a component which is directly detected, and the second type of binding ligand may be indirectly detected (e.g., via exposure to a precursor labeling agent). In another example, three types of binding ligands may be employed, wherein the first type of binding ligand associates with an analyte molecule and is directly or indirectly detectable, the second type of binding ligand associates with the analyte molecule, and the third type of binding ligand associates with the second type of binding ligand and is directly or indirectly detectable. The presence of both the first type of binding ligand and the third type of binding ligand in a location can be read as an "on" location.

At any point during an assay method of the present invention, at least one wash step may be carried out. The wash step may aid in the removal of any unbound binding ligands from the solution. For example, referring to FIG. 1, following association of the first type of binding ligand and the second type of binding ligand with respect to an analyte molecule (e.g., following step (B1) or step (C2), a wash step may be performed to remove any unbound binding ligands not immobilized with respect to an analyte molecule. The wash step may be performed using any suitable technique known to those of ordinary skill in the art. In embodiments where the assay employs magnetic beads (e.g., as capture objects to immobilize the analyte molecules), the beads may be isolated from the bulk solution with aid of a magnet.

The analyte molecules may be exposed to the at least two types of binding ligands under conditions such that a substantial fraction (e.g., at least about 70%, at least about 75%, at least about 80%, at least about 85%, at least about 90%, at least about 95%, at least about 97%, at least about 99%, or more) of the analyte molecules associate with at least one of each type of binding ligand. Non-limiting conditions which may be varied include the ratio of binding ligands to analyte molecules, the period of time of the exposure, the existence and/or type of physical confinement during incubation (e.g., exposure in bulk solution versus exposure at/in locations), agitation of the solution, and the like. In some cases, the binding ligands may be added to a solution comprising the plurality of analyte molecules. The ratio of binding ligands provided to analyte molecules in solution may be at least about 1:1, at least about 2:1, at least about 4:1, at least about 5:1, at least about 10:1, at least about 20:1, at least about 30:1, at least about 50:1, at least about 100:1, or greater. In some embodiments, the number/concentration of analyte molecules in the fluid sample is unknown and the number of binding ligands provided may be based on the maximum suspected number of analyte molecules in the fluid sample. In some cases, the solution may be agitated (e.g., stirred, shaken). A single analyte molecule may associate with more than one of each type of binding ligand (e.g., at least two, three, four, five, six, etc., of each type of binding ligand) in certain embodiments.

In some embodiments, the concentration of binding ligand used in an assay may be selected as to minimize certain events which may occur when an excess of binding ligand is present, for example, non-specific binding of the binding ligand. In some cases, if the concentration of binding ligand is too high, an increase in background readings may occur due to non-specific interactions (e.g., with the capture objects, reaction vessels, etc.). In some cases, the concentration of binding ligand may be selected (or estimated, in the case of an unknown concentration of analyte molecule) such that a only a fraction of the analyte molecules immobilized with respect to a capture object associate with a binding ligand (e.g., about 0.1%, about 1%, about 2%, about 3%, about 4%, about 5%, about 10%, about 20%, about 30%, about 40%, about 50%, or more). This may be especially useful in embodiments where the percentage of capture objects which associate with at least one analyte molecule is relatively high (e.g., greater than about 20%, greater than about 30%, greater than about 40%, greater than about 50%, greater than about 60%, greater than about 70%, greater than about 80%, greater than about 90%, or more). By providing the binding ligand at a lower concentration, in some cases, not every analyte molecule immobilized with respect to a capture object will associate with a binding ligand, which can be advantageous for quantification, for example when the presence of a binding ligand is required for detection, and especially when using a digital/binary read-out technique. For example, if the percentage of capture objects associated with an analyte molecule is about 50% or greater, a reduced number of binding ligands may be provided such that less than all of the immobilized analyte molecules associate with a binding ligand. In other cases, the percentage of binding ligands that associate with an analyte molecule may be reduced by decreasing the incubation time with the analyte molecule (e.g., limit the time of exposure such that only a fraction of the immobilized analyte molecules associate with an analyte molecule).

In some embodiments, a method for determining a measure of the concentration of analyte molecules in a fluid sample comprises providing the analyte molecules immobilized with respect to a binding surface having affinity for at least one type of analyte molecule, the binding surface forming (e.g., a surface of a well/reaction vessel on a substrate) or contained within (e.g., a surface of a capture object, such as a bead, contained within a well) one of a plurality of locations (e.g., a plurality of wells/reaction vessels) on a substrate (e.g., plate, dish, chip, optical fiber end, etc). The analyte molecules may be spatially segregated such that at least some of the plurality of locations contain at least one analyte molecule and a statistically significant fraction of the plurality of locations do not contain any analyte molecules, as described herein. At some point in the assay (e.g., prior to, concurrent with, or following the analyte molecules being immobilized with respect to the binding surface), the analyte molecules may be exposed to at least a first type of binding ligand having an affinity for a first epitope on the analyte molecules and a second type of binding ligand having an affinity for the first or a second epitope on the analyte molecules. As described herein, more than two types of binding ligand may be employed. At least a portion of the plurality of the locations may be addressed, and the number of the locations addressed which contain at least a first type of binding ligand and a second type of binding ligand can be determined. Based on at least this determination, a measure of the concentration of analyte molecules may be determined. In some cases, the binding surface comprises the surface of a bead contained within one of a plurality of locations on a substrate. In such cases, the exposing step may be performed prior to or following the bead being contained within one of the plurality of locations on the substrate. Non-limiting examples of assay methods/systems are described in U.S. patent application Ser. No. 12/731,130, entitled "Ultra-Sensitive Detection of Molecules or Particles using Beads or Other Capture Objects," by Duffy et al., filed Mar. 24, 2010; U.S. Patent Application No. 20070259448, entitled "Methods and arrays for target analyte detection and determination of target analyte concentration in solution," by Walt et al., filed Feb. 16, 2007; U.S. Patent Application No. 20070259385, entitled "Methods and arrays for detecting cells and cellular components in small defined volumes," by Walt et al., filed Feb. 16, 2007; U.S. Patent Application No. 20070259381, entitled "Methods and arrays for target analyte detection and determination of reaction components that affect a reaction," by Walt et al., filed Feb. 16, 2007; International Patent Application No. PCT/US07/019184, entitled "Methods for Determining the Concentration of an Analyte in Solution," by Walt et al., filed Aug. 20, 2007; and International Patent Application No. PCT/US09/005428, entitled "Ultra-Sensitive Detection of Molecules or Enzymes," by Duffy et al., filed Sep. 9, 2009, herein incorporated by reference.

Binding Ligands And Precursor Labeling Agents/Labeling Agent

Binding ligands may be selected from any suitable molecule, particle, or the like, as discussed more below, able to associate with an analyte molecule and/or to associate with another binding ligand. Certain binding ligands can comprise a component that is able to facilitate detection, either directly (e.g., via a detectable moiety) or indirectly. A component may facilitate indirect detection, for example, by converting a precursor labeling agent molecule into a labeling agent molecule (e.g., an agent that is detected in an assay). In some embodiments, the binding ligand may comprise an enzymatic component (e.g., horseradish peroxidase, beta-galactosidase, alkaline phosphatase, etc). A first type of binding ligand may be used in conjunction with additional binding ligands (e.g., second type, etc.), as discussed herein.

In some embodiments, and as described herein, more than one type of binding ligand may be used. In some embodiments, a first type of binding ligand and a second type of binding ligand may be provided. In some instances, at least two, at least three, at least four, at least five, at least eight, at least ten, or more, types of binding ligands may be provided. The binding ligands may be selected such that they interact with each other and/or an analyte molecule in a variety of different manners. Various examples of possible interactions are shown above in FIGS. 1-3.

In some embodiments, each type of binding ligand which is used for detection may be distinguishable from each of the other type of binding ligands used for detection and employed in the assay method. That is, each type of binding ligand which is directly or indirectly detected produces a signal which is distinguishable from the signals produced by the other types of binding ligand which are directly or indirectly detected. For example, the first type of binding ligand may comprise a first component (e.g., fluorescent entity) producing a first signal (e.g., a first fluorescence emission) and the second type of binding ligand may comprise a second component (e.g., fluorescent entity) producing a second signal (e.g., a second fluorescence emission), wherein the second signal is distinguishable from the first signal.

In some cases, however, each type of binding ligand which is directly or indirectly detected produces a signal which is the same as the signals produced by the other types of binding ligand which are directly or indirectly detected. In these embodiments, the detection of each type of binding ligand may be done sequentially so that the signals may be distinguished. For example, a first type of binding ligand may comprise a first enzymatic component and the second type of binding ligand may comprise a second type of enzymatic component. Both types of binding ligands may be immobilized with respect to an analyte molecule. The binding ligands may be exposed to a first type of precursor labeling agent, wherein the first type of precursor labeling agent is converted to a first type of labeling agent upon exposure to the first type of binding ligand. A first determination may be carried out to determine which reaction vessels contain a first type labeling agent. The binding ligands may be exposed to a second type of precursor labeling agent, wherein the second type of labeling agent is converted to a second type of labeling agent upon exposure to the second type of binding ligand. In some cases, the first type of labeling agent may be removed from the reaction vessels prior to exposure to a second type of precursor labeling agent (in some cases, a determination may be carried out to ensure that substantially all of the first type of labeling agent has been removed). The second type of labeling agent may produce a signal which is substantially the same as that produced by the first type of labeling agent. A second determination may be carried out to determine which reaction vessels contain the second type of labeling agent, and the first and second determination may be analyzed to determine which reaction vessels contained both the first type and the second type of labeling agent. As a specific example, the first type of binding ligand comprises first type of enzymatic component beta-galatosidase, and the first type of precursor labeling agent is resorufin-D-pyranogalactoside, whereas the second type of binding ligand comprises second type of enzymatic component, horseradish peroxidase, and the second type of precursor labeling agent is Amplex Red. Both precursor labeling agents are converted to a labeling agent which comprises resorufin, the moiety which is detectable.

The binding ligands may be detected directly or indirectly. In the case of direct detection, the binding ligands may comprise a molecule or moiety that may be directly interrogated and/or detected. Those of ordinary skill in the art will be aware of components that can be directly detected. For example, the component may be a fluorescent entity (e.g., a fluorescent moiety, fluorescent bead, etc.), a metal nanoparticle or nanocluster (e.g., a gold nanocluster or nanoparticle, silver nanocluster or nanoparticle), a quantum dot (e.g., CdSe quantum dot, CdTe quantum dot, etc.), or a radioactive isotope.

In some embodiments, the binding ligands may be indirectly detected. The indirect approach can include, for example, exposing a binding ligand associated with an analyte molecule to a precursor labeling agent, wherein the precursor labeling agent is converted into a labeling agent upon exposure to the binding ligand associated with an analyte molecule. The labeling agent may comprise a molecule or moiety that can be directly interrogated and/or detected. The presence or absence of a binding ligand at a location may then be determined by determining the presence or absence of a labeling agent at/in the location.

A non-limiting example of indirect detection is shown in FIG. 4. Analyte molecule 200 is associated with binding ligand 202. Binding ligand comprises a component 204 which is capable of converting precursor labeling agent molecule 206 into labeling agent 208, as indicated by arrow 207. Labeling agent 208 may be directly detected and used to determine the presence of binding ligand 202 at the location. Another non-limiting example was described above in FIG. 3, step (D).

In some embodiments, a binding ligand may comprise an enzymatic component. In this instance, the precursor labeling agent may be an enzymatic label, for example, a chromogenic, fluorogenic, or chemiluminescent enzymatic precursor labeling agent, that upon contact with the enzymatic component, converts to a labeling agent. In some cases, the chromogenic, fluorogenic, or chemiluminescent enzymatic precursor labeling agent is provided in an amount sufficient to contact every analyte molecule which was partitioned across a plurality of locations. In some cases, the enzymatic component may comprise beta-galactosidase, alkaline phosphatase, or horseradish peroxidase.

Other non-limiting examples of systems or methods for detection include embodiments where nucleic acid precursors are replicated into multiple copies or converted to a nucleic acid that can be detected readily, such as the polymerase chain reaction (PCR), rolling circle amplification (RCA), ligation, Loop-Mediated Isothermal Amplification (LAMP), etc. Such systems and methods will be known to those of ordinary skill in the art, for example, as described in "DNA Amplification: Current Technologies and Applications," Vadim Demidov et al., 2004.

As will be understood by those of ordinary skill in the art, a variety of appropriate chromogenic, fluorogenic, or chemiluminescent enzymatic precursor labeling agents may be selected for conversion by many different enzymes. Thus, any known chromogenic, fluorogenic, or chemiluminescent enzyme precursor labeling agent capable of producing a labeling agent in a reaction with a particular enzyme can potentially be used in the present invention as the precursor labeling agent in embodiments where the binding ligand comprises an enzymatic component. For example, many chromogenic, fluorogenic, or chemiluminescent precursor labeling agents suitable for use an enzymatic precursor labeling agent molecule are disclosed in *The Handbook—A Guide to Fluorescent Probes and Labeling Technologies*, Tenth Ed., Chapter 10.

In some embodiments, a first type of binding ligand may comprise a first type of enzymatic component and the second type of binding ligand may comprise a second type of enzymatic component which differs from the first type of enzymatic component. A capture object (e.g., a bead) comprising an analyte molecule, the first type of binding ligand, and the second type of binding ligand may be exposed to a first type of precursor labeling agent which is converted to a first type of labeling agent (e.g., comprising a first measurable property) upon exposure to the first type of enzymatic component and a second type of precursor labeling agent which is converted to a second type of labeling agent (e.g., comprising a measurable property which is distinguishable from the first measurable property) upon exposure to the second type of enzymatic component. Therefore, only locations which are determined to contain the first type of labeling agent and the second type of labeling agent are determined to contain a capture object carrying an analyte molecule. As described herein, however, in some cases, the first type of labeling agent and the second type of labeling agent may be the same or produce the same detectable signal, but be distinguished from each other via the time frame in which the signal is produced.

In some cases, the first type of binding ligand and the second type of binding ligand may each incorporate a component (e.g., such as a DNA label) and a third type of binding ligand may comprise two complimentary components to the components of the first type and second type of binding ligands (e.g., two types of complimentary DNA labels), wherein the third type of binding ligand also comprises an molecule or moiety for direct or indirect detection (e.g., the presence of the third type of binding ligand in a reaction vessel is required to determine the presence or absence of an analyte molecule in a location). Both the first type of binding ligand and the second types of binding ligand must be present in substantially close proximity to each other (e.g., via association with an analyte molecule) to allow for association of the third type of binding ligand, and therefore, for detection of the analyte molecule.

In certain embodiments, solubilized, or suspended precursor labeling agents may be employed, wherein the precursor labeling agents are converted to labeling agents which are insoluble in the liquid and/or which become immobilized within/near the location (e.g., within the reaction vessel in which the labeling agent is formed). Such precursor labeling agents and labeling agents and their use is described in commonly owned U.S. patent application Ser. No. 12/236,484, entitled "High Sensitivity Determination of the Concentration of Analyte molecules in a Fluid Sample," by Duffy et al., filed Sep. 23, 2008, incorporated herein by reference.

Methods and Systems for Segregating Analyte Molecules into Arrays of Locations

In certain embodiments, the assay methods of the present invention employ a step of spatially segregating a plurality of analyte molecules into a plurality of locations to facilitate detection/quantification, such that each location comprises/contains zero, one or more analyte molecules. Additionally, in some embodiments, the locations are provided in a manner such that each analyte molecule can be individually addressed. While numerous exemplary embodiments for spatially segregating a plurality of analyte molecules into a plurality of locations are described herein, numerous methods may be employed. Non-limiting examples of assay methods/systems are described in U.S. patent application Ser. No. 12/731,130, entitled "Ultra-Sensitive Detection of Molecules or Particles using Beads or Other Capture Objects," by Duffy et al., filed Mar. 24, 2010; U.S. Patent Application No. 20070259448, entitled "Methods and arrays for target analyte detection and determination of target analyte concentration in solution," by Walt et al., filed Feb. 16, 2007; U.S. Patent Application No. 20070259385, entitled "Methods and arrays for detecting cells and cellular components in small defined volumes," by Walt et al., filed Feb. 16, 2007; U.S. Patent Application No. 20070259381, entitled "Methods and arrays for target analyte detection and determination of reaction components that affect a reaction," by Walt et al., filed Feb. 16, 2007; International Patent Application No. PCT/US07/019184, entitled "Methods for Determining The Concentration of an Analyte In Solution," by Walt et al., filed Aug. 20, 2007; and International Patent Application No. PCT/US09/005428, entitled "Ultra-Sensitive Detection of Molecules or Enzymes," by Duffy et al., filed Sep. 9, 2009, herein incorporated by reference.

In some embodiments, the plurality of analyte molecules may be spatially segregated into a plurality of locations, wherein the locations comprise a plurality of reaction vessels. The analyte molecules may be partitioned across the plurality of reaction vessels such that at least some of the reaction vessels contain at least one analyte molecule and a statistically significant fraction of the reactions vessels contain no analyte molecules. A statistically significant fraction of reaction vessels that contain at least one analyte molecule (or no analyte molecules) will typically be able to be reproducibly detected and quantified using a particular system of detection and will typically be above the background noise (e.g., non-specific binding) that is determined when carrying out the assay with a sample that does not contain any analyte molecules, divided by the total number of locations addressed. A "statistically significant fraction" as used herein for the present embodiments, may be calculated according to the Equation 1:

$$n > 3\sqrt{n} \quad \text{(Eq. 1)}$$

wherein n is the number of determined events for a selected category of events. That is, a statistically significant fraction occurs when the number of events n is greater than three times square root of the number of events. For example, to determine a statistically significant fraction of the reaction vessels which contain an analyte molecule or particle, n is the number of reaction vessels which contain an analyte molecule. As another example, to determine a statistically significant fraction of capture objects associated with a single analyte molecule, n is the number of capture objects associated with a single analyte molecule.

In some embodiments, the statistically significant fraction of locations that contain at least one analyte molecule (or a single analyte molecule in some cases where the ratio of locations to analyte molecules would lead, statistically, to substantially only zero or one analyte molecule contained in each location) to the total number of locations containing sample is less than about 1:2, less than about 1:3, less than about 1:4, less than about 2:5, less than about 1:5, less than about 1:10, less than about 1:20, less than about 1:100, less than about 1:200, or less than about 1:500. In such embodiments, the fraction of locations not containing any analyte molecules to the total number of locations may be at least about 1:100, about 1:50, about 1:20, about 1:10, about 1:5, about 1:4, about 1:3, about 1:2, about 1:1, about 2:1, about 3:1, about 4:1, about 5:1, about 10:1, about 20:1, about 50:1, about 100:1, or more.

In some embodiments, the percentage of locations which contain at least one analyte molecule is less than about 50%, less than about 40%, less than about 30%, less than about 20%, less than about 10%, less than about 5%, less than about 2%, less than about 1%, less than about 0.5%, less than about 0.01%, or less, the total number of locations. In some embodiments, the percentage of locations which do not contain any analyte molecule is at least about 30%, at least about 40%, at least about 50%, at least about 60%, at least about 70%, at least about 80%, at least about 90%, at least about 95%, at least about 98%, or greater, the total number of locations.

In some embodiments, the assay methods may involve the use of a plurality of capture objects. The plurality of capture objects (e.g., beads) may be configured to capture an analyte molecule or particle. In some cases, the plurality of capture objects comprises a plurality of beads. The beads may or may not be magnetic. At least a portion of the capture objects may be spatially segregated into a plurality of locations (e.g., reaction vessels/wells). The plurality of analyte molecules may be exposed to a plurality of types of binding ligands prior to or following association of the plurality of analyte molecules with respect to the capture components. Various other aspects of assay methods using such capture components are described in commonly owned U.S. patent application Ser. No. 12/731,130, entitled "Ultra-Sensitive Detection of Molecules or Particles using Beads or Other Capture Objects" by Duffy et al., filed Mar. 24, 2010 incorporated by reference. Specifically, the methods and systems described herein may be used in combination with and in context with the single molecules methods and systems described in the above-referenced applications.

In some embodiments, a plurality of locations may be addressed and/or a plurality of capture objects and/or species/molecules/particles of interest may be detected substantially simultaneously. "Substantially simultaneously" when used in this context, refers to addressing/detection of the locations/capture objects/species/molecules/particles of interest at approximately the same time such that the time periods during which at least two locations/capture objects/species/molecules/particles of interest are addressed/detected overlap, as opposed to being sequentially addressed/detected, where they would not. Simultaneous addressing/detection can be accomplished by using various techniques, including optical techniques (e.g., CCD detector). Spatially segregating capture objects/species/molecules/particles into a plurality of discrete, resolvable locations, according to some embodiments facilitates substantially simultaneous detection by allowing multiple locations to be addressed substantially simultaneously. For example, for embodiments where individual species/molecules/particles are associated with capture objects that are spatially segregated with respect to the other capture objects into a plurality of discrete, separately resolvable locations during detection, substantially simultaneously addressing the plurality of discrete, separately resolvable locations permits individual capture objects, and thus individual species/molecules/particles (e.g., analyte molecules) to be resolved. For example, in certain embodiments, individual molecules/particles of a plurality of molecules/particles are partitioned across a plurality of reaction vessels such that each reaction vessel contains zero or only one species/molecule/particle. In some cases, at least about 80%, at least about 85%, at least about 90%, at least about 95%, at least about 96%, at least about 97%, at least about 98%, at least about 99%, at least about 99.5% of all species/molecules/particles are spatially separated with respect to other species/molecules/particles during detection. A plurality of species/molecules/particles may be detected substantially simultaneously within a time period of less than about 1 second, less than about 500 milliseconds, less than about 100 milliseconds, less than about 50 milliseconds, less than about 10 milliseconds, less than about 1 millisecond, less than about 500 microseconds, less than about 100 microseconds, less than about 50 microseconds, less than about 10 microseconds, less than about 1 microsecond, less than about 0.5 microseconds, less than about 0.1 microseconds, or less than about 0.01 microseconds, less than about 0.001 microseconds, or less. In some embodiments, the plurality of species/molecules/particles may be detected substantially simultaneously within a time period of between about 100 microseconds and about 0.001 microseconds, between about 10 microseconds and about 0.01 microseconds, or less.

During the addressing step of the method where the locations into which the capture objects/analyte molecules have been segregated are addressed, any of a variety of parameters may be determined. In some embodiments, the number of locations which contain both a first type of binding ligand and a second type of binding ligand is determined. The number of locations which do not contain both a first type of binding ligand and a second type of binding ligand may also be determined. A single interrogation or multiple interrogations of any subset or all of the locations ultimately addressed may be made at any given time to facilitate one or all of the above described determinations. The portion of locations addressed may be at least about 5%, or at least about 10%, or at least about 20%, or at least about 30%, or at least about 40%, or at least about 50%, or at least about 60%, or at least about 70%, or at least about 80%, or at least about 90%, or more of the total number of locations In some cases, the locations which contain the specified types of binding ligands may be determined by a single interrogation of the locations. In such embodiments, the detection system is configured such that it is able to detect and distinguish between each type of binding ligand. In some cases, however, the locations which contain each type of binding ligand may be determined by multiple interrogations of the locations. The multiple interrogations of each location may be combined/compared to determine which locations contain both binding ligands. For example, in some cases, a first interrogation of the locations may be conducted using light of a first range of wavelengths (e.g., a wavelength range where the first type of binding ligand produces a detectable fluorescence) to detect which locations contain a first type of binding ligand whereas a second interrogation is conducted using light of a second, differing range of wavelengths (e.g., a wavelength range where the second type of binding ligand produces a detectable fluorescence) to detect which locations contain a second type of binding ligand. The locations which contain both a first type of binding ligand and a second type of binding ligand may be determined by comparing/combining the results from the two interrogations for each location. It should be understood, however, that in some cases, a single type of binding ligand (e.g., a third type of binding ligand) may be detected to determine the presence of both a first type of binding ligand and a second type of binding ligand contained in a single location (e.g., in embodiments where a third type of binding ligand associates with an analyte molecule via association with both a first type of binding ligand and a second type of binding ligand, both immobilized with respect to an analyte molecule, and as outlined in FIG. 2).

In a specific embodiment of the present invention, the locations are optically interrogated. The locations exhibiting changes in their optical signature may be identified by a conventional optical train and optical detection system. Depending on the detected species (e.g., type of fluorescence entity, etc.) and the operative wavelengths, optical filters designed for a particular wavelength may be employed for optical interrogation of the locations. In embodiments where optical interrogation is used, the system may comprise more than one light source and/or a plurality of filters to adjust the wavelength and/or intensity of the light source. In some embodiments, the optical signal from a plurality of locations is determined using a CCD camera.

Other non-limiting examples of camera imaging types that can be used to capture images include charge injection devices (CIDs), complimentary metal oxide semiconductors (CMOSs) devices, scientific CMOS (sCMOS) devices, and time delay integration (TDI) devices, as will be known to those of ordinary skill in the art. The camera may be obtained from a commercial source. CIDs are solid state, two dimensional multi pixel imaging devices similar to CCDS, but differ in how the image is captured and read. For examples of CCDs, see U.S. Pat. No. 3,521,244 and U.S. Pat. No. 4,016,550. CMOS devices are also two dimensional, solid state imaging devices but differ from standard CCD arrays in how the charge is collected and read out. The pixels are built into a semiconductor technology platform that manufactures CMOS transistors thus allowing a significant gain in signal from substantial readout electronics and significant correction electronics built onto the device. For example, see U.S. Pat. No. 5,883,083). sCMOS devices comprise CMOS imaging technology with certain technological improvements that allows excellent sensitivity and dynamic range. TDI devices employ a CCD device which allows columns of pixels to be shifted into and adjacent column and allowed to continue gathering light. This type of device is typically used in such a manner that the shifting of the column of pixels is synchronous with the motion of the image being gathered such that a moving image can be integrated for a significant amount of time and is not blurred by the relative motion of the image on the camera. In some embodiments, a scanning mirror system coupled with a photodiode or photomultiplier tube (PMT) could be used to for imaging.

The plurality of locations may be formed using any suitable technique. In some embodiments, the plurality of locations comprises a plurality of reaction vessels/wells on a substrate. The reactions vessels, in certain embodiments, may be configured to receive and contain only a single capture object.

In some embodiments of the present invention, the plurality of reaction vessels may be sealed (e.g., after the introduction of the analyte molecules, binding ligands, and/or precursor labeling agent), for example, through the mating of the second substrate and a sealing component. The sealing of the reaction vessels may be such that the contents of each reaction vessel cannot escape the reaction vessel during the remainder of the assay. In some cases, the reaction vessels may be sealed after the addition of the analyte molecules and, optionally, at least one type of precursor labeling agent to facilitate detection of the analyte molecules. For embodiments employing precursor labeling agents, by sealing the contents in some or each reaction vessel, a reaction to produce the detectable labeling agents can proceed within the sealed reaction vessels, thereby producing a detectable amount of labeling agents that is retained in the reaction vessel for detection purposes.

The plurality of locations comprising a plurality of reaction vessels may be formed using a variety of methods and/or materials. In some cases, the plurality of reaction vessels is formed as an array of depressions on a first surface. In other cases, however, the plurality of reaction vessels may be formed by mating a sealing component comprising a plurality of depressions with a substrate that may either have a featureless surface or include depressions aligned with those on the sealing component. Any of the device components, for example, the substrate or sealing component, may be fabricated from a compliant material, e.g., an elastomeric polymer material, to aid in sealing. The surfaces may be or made to be hydrophobic or contain hydrophobic regions to minimize leakage of aqueous samples from the microwells.

In some cases, the sealing component may be capable of contacting the exterior surface of an array of microwells (e.g., the cladding of a fiber optic bundle as described in more detail below) such that each reaction vessel becomes sealed or isolated such that the contents of each reaction vessel cannot escape the reaction vessel. According to one embodiment, the sealing component may be a silicone elastomer gasket that may be placed against an array of microwells with application of substantially uniform pressure across the entire substrate. In some cases, the reaction vessels may be sealed after the addition of the plurality of capture objects used for analyte capture and, optionally, any precursor labeling agent molecule that may be used to facilitate detection of the analyte molecule.

Figure 5:
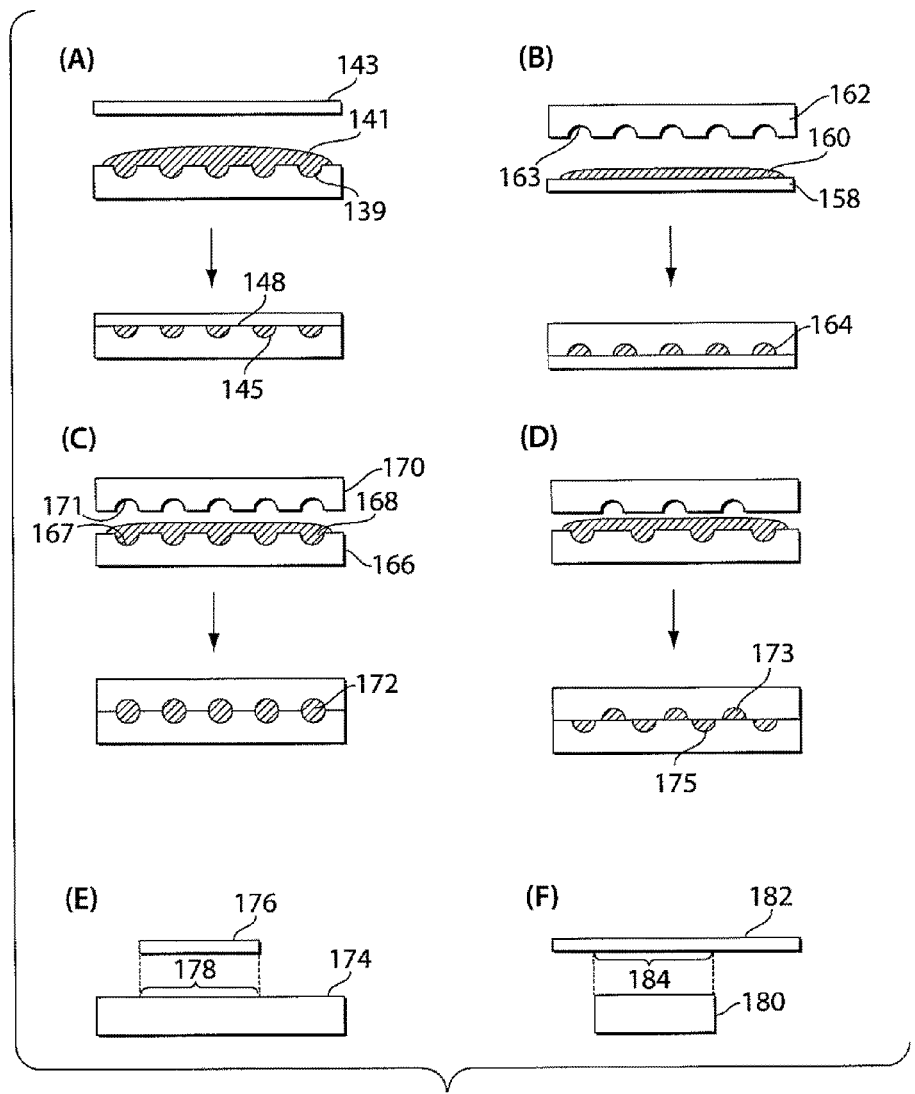
FIG. 5 is a schematic flow diagram depicting an embodiment of a method (steps A-D) for the formation of a plurality of reaction vessels through mating of a substrate and a sealing component and depicting examples of the size (E, F) of a sealing component relative to a substrate.

A non-limiting example of the formation of a plurality of reaction vessels containing assay solution on/in a substrate is depicted in FIG. 5. FIG. 5, panel (A) shows a surface comprising a plurality of microwells 139, which have been exposed to an assay solution 141 (e.g., a solution containing the analyte molecules), and a sealing component 143. Sealing component 143 in this example comprises a substantially planar bottom surface. Mating of substrate 139 with sealing component 143 forms a plurality of sealed reaction vessels 145. The areas between the reaction vessels 148 may be modified to aid in the formation of a tight seal between the reaction vessels.

A second embodiment is shown in FIG. 5, panel (B), in which sealing component 162 comprising a plurality of microwells 163 is mated with a substantially planar surface 158 which has been exposed to assay solution 162, thereby forming a plurality of reaction vessels 164.

In a third embodiment, as shown in FIG. 5, panel (C), substrate surface 166 comprising a plurality of microwells 167 is mated with sealing component 170 also comprising a plurality of microwells 171. In this embodiment, the microwells in the substrate and the microwells in the sealing components are substantially aligned so each reaction vessel 172 formed comprises a portion of the microwell from the sealing component and a portion of a microwell from the substrate. In FIG. 5, panel (D), the microwells are not aligned such that each reaction vessel comprises either a microwell from the sealing component 173 or a microwell from the substrate 175.

The sealing component may be essentially the same size as the substrate or may be different in size. In some cases, the sealing component is approximately the same size as the substrate and mates with substantially the entire surface of the substrate. In other cases, as depicted in FIG. 5, panel (E), the sealing component 176 is smaller than the substrate 174 and the sealing component only mates with a portion 178 of the substrate.

In yet another embodiment, as depicted in FIG. 5, panel (F), the sealing component 182 is larger than the substrate 180, and only a portion 184 of the sealing component mates with the substrate 180.

In some embodiments, the reaction vessels may all have approximately the same volume. In other embodiments, the reaction vessels may have differing volumes. The volume of each individual reaction vessel may be selected to be appropriate to facilitate any particular assay protocol. For example, in one set of embodiments where it is desirable to limit the number of capture objects used for analyte capture contained in each vessel to a small number, the volume of the reaction vessels may range from attoliters or smaller to nanoliters or larger depending upon the nature of the capture objects, the detection technique and equipment employed, the number and density of the wells on the substrate and the expected concentration of capture objects in the fluid applied to the substrate containing the wells. In one embodiment, the size of the reaction vessel may be selected such only a single capture object used for analyte capture can be fully contained within the reaction vessel.

In accordance with one embodiment of the present invention, the reaction vessels may have a volume between about the reaction vessels may have a volume between about 1 femtoliter and about 1 picoliter, between about 1 femtoliters and about 100 femtoliters, between about 10 attoliters and about 100 picoliters, between about 1 picoliter and about 100 picoliters, between about 1 femtoliter and about 1 picoliter, or between about 30 femtoliters and about 60 femtoliters. In some cases, the reaction vessels have a volume of less than about 1 picoliter, less than about 500 femtoliters, less than about 100 femtoliters, less than about 50 femtoliters, or less than about 1 femtoliter. In some cases, the reaction vessels have a volume of about 10 femtoliters, about 20 femtoliters, about 30 femtoliters, about 40 femtoliters, about 50 femtoliters, about 60 femtoliters, about 70 femtoliters, about 80 femtoliters, about 90 femtoliters, or about 100 femtoliters.

The total number of locations and/or density of the locations employed in an assay (e.g., the number/density of reaction vessels in an array) can depend on the composition and end use of the array. For example, the number of reaction vessels employed may depend on the number of types of analyte molecule and/or binding ligand employed, the suspected concentration range of the assay, the method of detection, the size of the capture objects, the type of detection entity (e.g., free labeling agent in solution, precipitating labeling agent, etc.). Arrays containing from about 2 to many billions of reaction vessels (or total number of reaction vessels) can be made by utilizing a variety of techniques and materials. Increasing the number of reaction vessels in the array can be used to increase the dynamic range of an assay or to allow multiple samples or multiple types of analyte molecules to be assayed in parallel. The array may comprise between one thousand and one million reaction vessels per sample to be analyzed. In some cases, the array comprises greater than one million reaction vessels. In some embodiments, the array comprises between about 1,000 and about 50,000, between about 1,000 and about 1,000,000, between about 1,000 and about 10,000, between about 10,000 and about 100,000, between about 100,000 and about 1,000,000, between about 100,000 and about 500,000, between about 1,000 and about 100,000, between about 50,000 and about 100,000, between about 20,000 and about 80,000, between about 30,000 and about 70,000, between about 40,000 and about 60,000, reaction vessels. In some embodiments, the array comprises about 10,000, about 20,000, about 50,000, about 100,000, about 150,000, about 200,000, about 300,000, about 500,000, about 1,000,000, or more, reaction vessels.

The array of reaction vessels may be arranged on a substantially planar surface or in a non-planar three-dimensional arrangement. The reaction vessels may be arrayed in a regular pattern or may be randomly distributed. In a specific embodiment, the array is a regular pattern of sites on a substantially planar surface permitting the sites to be addressed in the X-Y coordinate plane.

In some embodiments, the reaction vessels are formed in a solid material. As will be appreciated by those in the art, the number of potentially suitable materials in which the reaction vessels can be formed is very large, and includes, but is not limited to, glass (including modified and/or functionalized glass), plastics (including acrylics, polystyrene and copolymers of styrene and other materials, polypropylene, polyethylene, polybutylene, polyurethanes, cyclic olefin copolymer (COC), cyclic olefin polymer (COP), Teflon®, polysaccharides, nylon or nitrocellulose, etc.), elastomers (such as poly(dimethyl siloxane) and poly urethanes), composite materials, ceramics, silica or silica-based materials (including silicon and modified silicon), carbon, metals, optical fiber bundles, or the like. In general, the substrate material may be selected to allow for optical detection without appreciable autofluorescence. In certain embodiments, the reaction vessels may be formed in a flexible material.

A reaction vessel in a surface (e.g., substrate or sealing component) may be formed using a variety of techniques known in the art, including, but not limited to, photolithography, stamping techniques, molding techniques, etching techniques, or the like. As will be appreciated by those of the ordinary skill in the art, the technique used can depend on the composition and shape of the supporting material and the size and number of reaction vessels.

In a particular embodiment, an array of reaction vessels is formed by creating microwells in an end of a fiber optic bundle and utilizing a planar compliant surface as a sealing component. In certain such embodiments, an array of reaction vessels in the end of a fiber optic bundle may be formed as follows. First, an array of microwells is etched into the end of a polished fiber optic bundle. Techniques and materials for forming and etching a fiber optic bundle are known to those of ordinary skill in the art. For example, the diameter of the optical fibers, the presence, size and composition of core and cladding regions of the fiber, and the depth and specificity of the etch may be varied by the etching technique chosen so that microwells of the desired volume may be formed. In certain embodiments, the etching process creates microwells by preferentially etching the core material of the individual glass fibers in the bundle such that each well is approximately aligned with a single fiber and isolated from adjacent wells by the cladding material. Potential advantages of the fiber optic array format is that it can produce thousands to millions of reaction vessels without complicated microfabrication procedures and that it can provide the ability to observe and optically address many reaction vessels simultaneously.

Each microwell may be aligned with an optical fiber in the bundle so that the fiber optic bundle can carry both excitation and emission light to and from the wells, enabling remote interrogation of the well contents. Further, an array of optical fibers may provide the capability for simultaneous or non-simultaneous excitation of molecules in adjacent vessels, without signal "cross-talk" between fibers. That is, excitation light transmitted in one fiber does not escape to a neighboring fiber.

Alternatively, the equivalent structures of a plurality of reaction vessels may be fabricated using other methods and materials that do not utilize the ends of an optical fiber bundle as a substrate. For example, the array may be a spotted, printed or photolithographically fabricated substrate produced by techniques known in the art; see for example WO95/25116; WO95/35505; PCT US98/09163; U.S. Pat. Nos. 5,700,637, 5,807,522, 5,445,934, 6,406,845, and 6,482,593. In some cases, the array may be produced using molding, embossing, and/or etching techniques as will be known to those of ordinary skill in the art.

In certain embodiments, the present invention provides a system equipped with a mechanical platform that applies a sealing component to a substrate. The platform may be positioned beneath a stage on the system. After the chosen reaction components have been added to an array of reaction vessels, the sealing component may be mated with the array. For example, the sealing component may be sandwiched between a flat surface (such as, for example, a microscope slide) and the array of reaction vessels using uniform pressure applied by the mechanical platform.

Figure 6A:
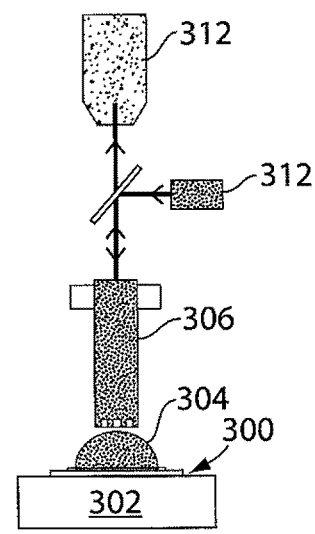
FIG. 6A depicts an experimental set-up for detection using light, according to one embodiment of the present invention.
Figure 6B:
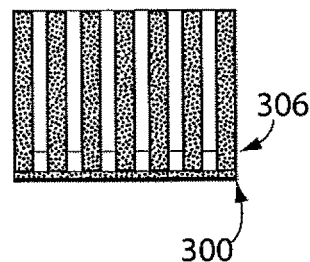
FIG. 6B shows a fiber optic array that has been sealed with a sealing component, according to one embodiment.

A non-limiting embodiment is illustrated in FIG. 6A. A sealing component 300 is placed on top of mechanical platform 302. The assay solution 304 is placed on top of the sealing component 300. The mechanical platform is moved upwards towards the array 306 (e.g., fiber optic array) such that uniform pressure is applied. As shown in FIG. 6B, the sealing component 300 forms a tight seal with the array 306. In other instances, varying pressure may be applied to the sealing component to form a tight seal between the sealing component and the array. The system may also comprise additional components 312 that may be utilized to analyze the array (e.g., microscope, computer, etc.) as discussed more herein.

In some embodiments, the plurality of locations may not comprise a plurality of reaction vessels/wells. For example, in embodiments where capture objects are employed, a patterned substantially planar surface may be employed and the patterned areas form a plurality of locations. In some cases, the patterned areas may comprise substantially hydrophilic surfaces which are substantially surrounded by substantially hydrophobic surfaces. In certain embodiments, a plurality of capture objects (e.g., beads) may be substantially surrounded by a substantially hydrophilic medium (e.g., comprising water), and the beads may be exposed to the patterned surface such that the beads associate in the patterned areas (e.g., the hydrophilic locations on the surface), thereby spatially segregating the plurality of beads. For example, in one such embodiment, a substrate may be or include a gel or other material able to provide a sufficient barrier to mass transport (e.g., convective and/or diffusional barrier) to prevent capture objects used for analyte capture and/or precursor labeling agent and/or labeling agent from moving from one location on or in the material to another location so as to cause interference or cross-talk between spatial locations containing different capture objects during the time frame required to address the locations and complete the assay. For example, in one embodiment, a plurality of capture objects is spatially separated by dispersing the capture objects on and/or in a hydrogel material. In some cases, a precursor labeling agent may be already present in the hydrogel, thereby facilitating development of a local concentration of the labeling agent (e.g., upon exposure to a binding ligand or analyte molecule carrying an enzymatic component). As still yet another embodiment, the capture objects may be confined in one or more capillaries. In some cases, the plurality of capture objects may be absorbed or localized on a porous or fibrous substrate, for example, filter paper. In some embodiments, the capture objects may be spatially segregated on a uniform surface (e.g., a planar surface), and the capture objects may be detected using precursor labeling agents which are converted to substantially insoluble or precipitating labeling agents that remain localized at or near the location of where the corresponding capture object is localized. The use of such substantially insoluble or precipitating labeling agents is described herein. In some cases, single analyte molecules may be spatially segregated into a plurality of droplets. That is, single analyte molecules may be substantially contained in a droplet containing a first fluid. The droplet may be substantially surrounded by a second fluid, wherein the second fluid is substantially immiscible with the first fluid.

Quantification

According to some embodiments of the present invention, the methods, systems, and/or devices are used to determine the presence and/or a measure of the concentration of a plurality of analyte molecules (or particles) in a fluid sample based at least in part on detecting and/or quantifying at least some of a plurality of locations comprising at least a first type of binding ligand and a second type of binding ligand. In some cases, the concentration of the analyte molecules in a fluid sample may be linearly proportional to the number of locations determined to contain at least a first type of binding ligand and a second type of binding ligand. In other cases, the measure of concentration of the analyte molecules in a fluid sample may be related to the determination and/or quantification of the number of locations containing at least a first type of binding ligand and a second type of binding ligand by a non-linear relationship. In some embodiments, a measure of the concentration of analyte molecules in a fluid sample may be determined at least in part using a calibration curve. Methods to determine a measure of the concentration of analyte molecules in a fluid sample are discussed more below. In some cases, methods for determining a measure of the concentration of analyte molecules in a fluid same may be carried out according to the methods described in U.S. patent application Ser. No. 12/731,130, entitled "Ultra-Sensitive Detection of Molecules or Particles using Beads or Other Capture Objects," by Duffy et al., filed Mar. 23, 2010.

In some embodiments, additional determinations may be carried out. In some cases, the number of locations which do not comprise at least a first type of binding ligand and a second type of binding ligand (e.g., locations which contain only a first type of binding ligand or a second type of binding ligand, or no binding ligands). In these cases, a measure of the concentration of analyte molecules in a fluid sample may be based on the ratio of locations comprising at least a first type of binding ligand and a second type of binding ligand, to the number of locations comprising which do not contain at least a first type of binding ligand and a second type of binding ligand.

In certain embodiments, the fraction of locations (e.g., the statistically significant fraction) which comprises a single analyte molecule (e.g., associated with at least a first type of binding ligand and a second type of binding ligand) is less than about 50%, less than about 40%, less than about 25%, less than about 10%, less than about 5%, less than about 1%, less than about 0.5%, or less than about 0.1% of the total number of locations (e.g., in some cases, containing a capture object). In some cases, the percentage of locations which do not contain at least a first type of binding ligand and a second type of binding ligand is at least about 20%, at least about 40%, at least about 50%, at least about 60%, at least about 70%, at least about 75%, at least about 80%, at least about 90%, or at least about 95%, at least about 99%, at least about 99.5%, at least about 99.9%, or greater, of the total number of locations.

According to one embodiment, the quantification method of the present invention can be performed as follows. A fluid sample containing or suspected of containing an analyte molecule of interest is contacted with one or more types of binding ligands (and optionally, a plurality of capture objects) and the analyte molecules (or capture objects) are partitioned across an array of locations, such as reaction vessels/wells (as described previously). In some embodiments, where a binary read-out method is desired to be used for determination, in the step of contacting the fluid sample with the locations, the relative amounts/concentrations of fluid sample and number of locations may be selected (e.g., based on a known or estimated/suspected approximate concentration range of analyte molecules in the sample) so that the ratio of analyte molecules in the fluid sample to total number of locations is less than about 1:5, less than about 1:10, less than about 1:12, less than about 1:15, less than about 1:20, less than about 1:50, less than about 1:100, or less. With such ratios, at least some of the locations statistically will be expected to contain a single analyte molecule and the majority of the remainder of the locations will not contain any analyte molecules. The number of locations containing multiple analyte molecules under such conditions may be low enough to be neglected, such that locations determined to comprise an analyte molecule can be assumed to comprise a single analyte molecule. Under such conditions, an analysis system configured to perform a binary read out quantification may be used to determine the number of locations which comprise an analyte molecule by any detection method as described herein (e.g., by detecting the presence of more than one type of binding ligand in the reaction vessel). The number of locations which comprise an analyte molecule capture object associated with an analyte molecule is then counted. Utilization of a zero (no analyte molecule detected) or one (an analyte molecule detected) response, in conjunction with using an array with a large number of locations can permit a determination of bulk concentrations of analyte molecules in the sample by counting the actual number of molecules contained in the volume of sample partitioned across and contained in the locations.

In some assays, a Poisson distribution adjustment may be applied to numbers and/or ratios determined by a binary read-out method to facilitate and/or improve accuracy of determining a concentration of analyte molecules in a fluid sample. For example, in embodiments where the ratio of analyte molecules in the fluid sample to the total number of capture objects contacted with the fluid sample is greater than about 1:10, greater than about 1:5, greater than about 1:4, greater than about 1:3, or greater than about 1:2, or between about 1:10 and about 1:2, between about 1:5 and about 1:2, the number of analyte molecules immobilized per capture may be zero or one, with a greater proportion containing more than one than for the regime described in the paragraph above. In some such cases, performance and accuracy of the concentration determinations may be improved over use of an assumption that all positive locations contain only a single analyte molecule (as described in the paragraph above) by employing a Poisson distribution adjustment to predict the number of locations expected to contain 0, 1, 2, 3, 4, etc., analyte molecules (e.g., per capture object). Poisson distribution adjustment will be known to those of ordinary skill in the art. For example, see U.S. patent application Ser. No. 12/731,130, entitled "Ultra-Sensitive Detection of Molecules or Particles using Beads or Other Capture Objects" by Duffy et al., filed Mar. 24, 2010

In some embodiments, a measure of the concentration of analyte molecules or particles in the fluid sample may be determined at least in part by comparison of a measured parameter to a calibration standard. For example, the number and/or fraction of locations that comprise an analyte molecule associated with at least a first type of binding ligand and a second type of binding ligand (e.g., based on a binary read-out) may be calibrated against a calibration curve to determine a measure of the concentration of the analyte molecule in the fluid sample. The calibration curve may be produced by completing the assay with a plurality of standardized samples of known concentration under substantially similar conditions as those used to analyze a test sample with unknown concentration. A reading may be taken for the signal related to the detection/quantification of the analyte molecule associated with at least a first type of binding ligand and a second type of binding ligand for each standardized sample, therefore allowing for the formation of a calibration curve relating the detection of the analyte molecules associated with a first type of binding ligand and a second type of binding ligand with a known concentration of the analyte molecule. The assay may then be completed on a sample containing the analyte molecule in an unknown concentration, and the detection of the analyte molecule associated with at least a first type of binding ligand and a second type of binding ligand from this assay may be compared to the calibration curve to determine a measure of the concentration of the analyte molecule in the fluid sample.

In some embodiments, the concentration of analyte molecules in the fluid sample may be determined through use of a calibration curve using an assay system employing a computer. The computer may execute software that may use the data collected to produce the calibration curve and/or to determine a measure of the concentration of analyte molecules in a test fluid sample from such calibration curve. For example, a fluorescence image of an array comprising the plurality of capture objects partitioned across the array may be collected and analyzed using image analysis software (e.g., IP Lab, BD Biosciences). The analysis software may automatically calculate the number of locations that have fluorescence intensity over the background intensity (e.g., a number that correlates to the number of locations which comprise both a first type of binding ligand and a second type of binding ligand). The number of locations which comprise fluorescence intensity over the background intensity may be divided by the total number of locations addressed, for example, to determine the fraction of locations which comprise an analyte molecule. The active location fraction may be compared to a calibration curve to determine a measure of the concentration of analyte molecules in the fluid sample.

In certain embodiments, it may be possible to increase both the dynamic range and the sensitivity of the assay by expanding the number of locations into which the capture objects are partitioned and/or by adjusting the ratio of capture objects (e.g. beads) to analyte molecules in the initial capture step. In certain cases, decreasing or increasing the analyte-to bead ratio may result in more dynamic range. In some cases, as the volume of a sample increases, detecting small numbers of analyte molecule with accuracy, may, in some cases, become more challenging for example, due to limitations of equipment, time constraints, etc. For example, to achieve the same efficiencies in larger volume sample (e.g., 1 mL, 10 mL) as achieved with a smaller volume sample (e.g., 100 µL), more beads (e.g., 10 and 100 times more beads, respectively) may be necessary, and thus, the beads may need to be spatially segregated into larger number of locations, wherein the larger number of locations may require an increased imaging area.

For the capture step, the choice of bead concentration may depend on several competing factors. For example, it can be advantageous if sufficient beads are present to capture most of the target analyte from thermodynamic and kinetic perspectives. As an exemplary illustration, thermodynamically, 200,000 beads in 100 µL that each have about 80,000 capture components (e.g. antibodies) bound to correlates to an antibody concentration of about 0.3 nM, and the antibody-protein equilibrium at that concentration may give rise to a relatively high capture efficiency of target analyte molecules in certain cases (e.g. >70%). Kinetically, for 200,000 beads dispersed in 100 µL, the average distance between beads can be estimated to be about 80 µm. Proteins the size of TNF-α and PSA (17.3 and 30 kDa, respectively), as exemplary analyte molecules, for example, will typically tend to diffuse 80 µm in less than 1 min, such that, over a 2 hour incubation, capture of such analyte molecules will tend not to be limited kinetically. In addition, it can also be advantageous to provide sufficient beads loaded onto the arrays to limit Poisson noise to a desired or acceptable amount. Considering as an example a situation where 200,000 beads in a in 10 µL volume are loaded onto an array, typically about 20,000-30,000 beads may become trapped in femtoliter sized wells of the array. For a typical background signal (e.g. due to non specific binding, etc.) of 1% active beads, this loading would be expected to result in a background signal of 200-300 active beads detected, corresponding to a coefficient of variation (CV) from Poisson noise of 6-7%, which may be acceptable in typical embodiments. However, bead concentrations above certain concentrations may be undesirable in certain cases in that they may lead to: a) increases in non-specific binding that may reduce signal-to-background; and/or b) undesirably low ratios of analyte-to-bead such that the fraction of active beads is too low, resulting in high CVs from Poisson noise. In certain embodiments, considering a balance of factors such as those discussed above, providing about 200,000 to 1,000,000 beads per 100 µL of test sample may be desirable or, in certain cases optimal, for performing certain assays of the invention.

For embodiments of the inventive assay employing one or more binding ligand(s) to label the captured analyte molecules, it may be advantageous to, in certain instances, adjust the concentrations used to yield desirable or optimal performance. For example, considering an embodiment involving an analyte molecule that is a protein (captured protein) and employing a first binding ligand comprising a detection antibody and a second binding ligand comprising an enzyme conjugate (e.g. SβG), the concentrations of detection antibody and enzyme conjugate (SβG) used to label the captured protein may in some cases be limited or minimized to yield an acceptable background signal (e.g. 1% or less) and Poisson noise. The choice of the concentrations of detection antibody and enzyme conjugate (SβG) used to label the captured protein can be factors in improving the performance of or optimizing certain of the inventive assay methods. In certain cases, it may be desirable for only a fraction of the capture proteins to be labeled so as to avoid saturating signals produced by the assay. For example, for a particular assay where background levels observed are equivalent to ~1-2 fM of target protein, such that the ratio of analyte to bead may be about 0.3-0.6, the number of active beads may be in the range of about 25-40% if every protein was labeled with an enzyme, which may be higher than desirable in some cases. To produce background signals that may be closer to a lower end of the dynamic range for a digital detection assay—considering e.g. that in certain cases 1% active beads may provide a reasonable noise floor for background in digital detection assays of the invention—appropriate labeling of the captured protein can potentially be achieved by kinetic control of the labeling steps, either by limiting or minimizing the concentrations of both labeling reagents or by using shorter incubation times. For example, in an embodiment where label concentrations are minimized, use of a standard ELISA incubation time may provide acceptable results; e.g. using a total assay time of ~6 h. This length of time may be acceptable for testing that tolerates a daily turnaround time for samples. For shorter turnaround times of, for example, <1 hour (e.g., for point-of-care applications), the assay could be performed with shorter incubations with higher concentrations of labels.

In some embodiments, the concentration of analyte molecules or particles in the fluid sample that may be substantially accurately determined is less than about 5000 fM, less than about 3000 fM, less than about 2000 fM, less than about 1000 fM, less than about 500 fM, less than about 300 fM, less than about 200 fM, less than about 100 fM, less than about 50 fM, less than about 25 fM, less than about 10 fM, less than about 5 fM, less than about 2 fM, less than about 1 fM, less than about 500 aM (attomolar), less than about 100 aM, less than about 10 aM, less than about 5 aM, less than about 1 aM, less than about 0.1 aM, less than about 500 zM (zeptomolar), less than about 100 zM, less than about 10 zM, less than about 5 zM, less than about 1 zM, less than about 0.1 zM, or less. In some cases, the limit of detection (e.g., the lowest concentration of an analyte molecule which may be determined in solution substantially accurately) is about 100 fM, about 50 fM, about 25 fM, about 10 fM, about 5 fM, about 2 fM, about 1 fM, about 500 aM (attomolar), about 100 aM, about 50 aM, about 10 aM, about 5 aM, about 1 aM, about 0.1 aM, about 500 zM (zeptomolar), about 100 zM, about 50 zM, about 10 zM, about 5 zM, about 1 zM, about 0.1 zM, or less. In some embodiments, the concentration of analyte molecules or particles in the fluid sample that may be substantially accurately determined is between about 5000 fM and about 0.1 fM, between about 3000 fM and about 0.1 fM, between about 1000 fM and about 0.1 fM, between about 1000 fM and about 0.1 zM, between about 100 fM and about 1 zM, between about 100 aM and about 0.1 zM.

The concentration of analyte molecules or particles in a fluid sample may be considered to be substantially accurately determined if the measured concentration of the analyte molecules or particles in the fluid sample is within about 10% of the actual (e.g., true) concentration of the analyte molecules or particles in the fluid sample. In certain embodiments, the measured concentration of the analyte molecules or particles in the fluid sample may be within about 5%, within about 4%, within about 3%, within about 2%, within about 1%, within about 0.5%, within about 0.4%, within about 0.3%, within about 0.2% or within about 0.1%, of the actual concentration of the analyte molecules or particles in the fluid sample. In some cases, the measure of the concentration determined differs from the true (e.g., actual) concentration by no greater than about 20%, no greater than about 15%, no greater than 10%, no greater than 5%, no greater than 4%, no greater than 3%, no greater than 2%, no greater than 1%, or no greater than 0.5%. The accuracy of the assay method may be determined, in some embodiments, by determining the concentration of analyte molecules in a fluid sample of a known concentration using the selected assay method.

Exemplary Target Analytes

As will be appreciated by those in the art, a large number of analyte molecules and particles may be detected and, optionally, quantified using methods and systems of the present invention; basically, any analyte molecule that is able to be made to become immobilized with respect to a binding ligand can be potentially investigated using the invention. Certain more specific targets of potential interest that may comprise an analyte molecule are mentioned below. The list below is exemplary and non-limiting.

In some embodiments, the analyte molecule may be a biomolecule. Non-limiting examples of biomolecules include hormones, antibodies, cytokines, proteins, nucleic acids, lipids, carbohydrates, lipids cellular membrane antigens and receptors (neural, hormonal, nutrient, and cell surface receptors) or their ligands, or combinations thereof. Non-limiting embodiments of proteins include peptides, polypeptides, protein fragments, protein complexes, fusion proteins, recombinant proteins, phosphoproteins, glycoproteins, lipoproteins, or the like. As will be appreciated by those in the art, there are a large number of possible proteinaceous analyte molecules that may be detected or evaluated for binding partners using the present invention. In addition to enzymes as discussed above, suitable protein analyte molecules include, but are not limited to, immunoglobulins, hormones, growth factors, cytokines (many of which serve as ligands for cellular receptors), cancer markers, etc. Non-limiting examples of biomolecules include PSA and TNF-alpha.

In certain embodiments, the analyte molecule may be a host-translationally modified protein (e.g., phosphorylation, methylation, glycosylation) and the capture component may be an antibody specific to a post-translational modification. Modified proteins may be captured with capture components comprising a multiplicity of specific antibodies and then the captured proteins may be further bound to a binding ligand comprising a secondary antibody with specificity to a post-translational modification. Alternatively, modified proteins may be captured with capture components comprising an antibody specific for a post-translational modification and then the captured proteins may be further bound to binding ligands comprising antibodies specific to each modified protein.

In another embodiment, the analyte molecule is a nucleic acid. A nucleic acid may be captured with a complementary nucleic acid fragment (e.g., an oligonucleotide) and then optionally subsequently labeled with a binding ligand comprising a different complementary oligonucleotide.

Suitable analyte molecules and particles include, but are not limited to small molecules (including organic compounds and inorganic compounds), environmental pollutants (including pesticides, insecticides, toxins, etc.), therapeutic molecules (including therapeutic and abused drugs, antibiotics, etc.), biomolecules (including hormones, cytokines, proteins, nucleic acids, lipids, carbohydrates, cellular membrane antigens and receptors (neural, hormonal, nutrient, and cell surface receptors) or their ligands, etc), whole cells (including prokaryotic (such as pathogenic bacteria) and eukaryotic cells, including mammalian tumor cells), viruses (including retroviruses, herpesviruses, adenoviruses, lentiviruses, etc.), spores, etc.

In some embodiments, the analyte molecule may be an enzyme. Non-limiting examples of enzymes include an oxidoreductase, transferase, kinase, hydrolase, lyase, isomerase, ligase, and the like. Additional examples of enzymes include, but are not limited to, polymerases, cathepsins, calpains, amino-transferases such as, for example, AST and ALT, proteases such as, for example, caspases, nucleotide cyclases, transferases, lipases, enzymes associated with heart attacks, and the like. When a system/method of the present invention is used to detect the presence of viral or bacterial agents, appropriate target enzymes include viral or bacterial polymerases and other such enzymes, including viral or bacterial proteases, or the like.

In other embodiments, the analyte molecule may comprise an enzymatic component. For example, the analyte particle can be a cell having an enzyme or enzymatic component present on its extracellular surface. Alternatively, the analyte particle is a cell having no enzymatic component on its surface. Such a cell is typically identified using an indirect assaying method described below. Non-limiting example of enzymatic components are horseradish peroxidase, beta-galactosidase, and alkaline phosphatase.

The fluid sample containing or suspected of containing an analyte molecule may be derived from any suitable source. In some cases, the sample may comprise a liquid, fluent particulate solid, fluid suspension of solid particles, supercritical fluid, and/or gas. In some cases, the analyte molecule may be separated or purified from its source prior to determination; however, in certain embodiments, an untreated sample containing the analyte molecule may be tested directly. The source of the analyte molecule may be synthetic (e.g., produced in a laboratory), the environment (e.g., air, soil, etc.), a mammal, an animal, a plant, or any combination thereof. In a particular example, the source of an analyte molecule is a human bodily substance (e.g., blood, serum, plasma, urine, saliva, tissue, organ, or the like). The volume of the fluid sample analyzed may potentially be any amount within a wide range of volumes, depending on a number of factors such as, for example, the number of capture objects used/available, the number of locations us/available, etc. In a few particular exemplary embodiments, the sample volume may be about 0.01 ul, about 0.1 uL, about 1 uL, about 5 uL, about 10 uL, about 100 uL, about 1 mL, about 5 mL, about 10 mL, or the like. In some cases, the volume of the fluid sample is between about 0.01 uL and about 10 mL, between about 0.01 uL and about 1 mL, between about 0.01 uL and about 100 uL, or between about 0.1 uL and about 10 uL.

In some cases, the fluid sample may be diluted prior to use in an assay. For example, in embodiments where the source of an analyte molecule is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, or greater, prior to use. The sample may be added to a solution comprising the plurality of capture objects, or the plurality of capture objects may be added directly to or as a solution to the sample.

Capture Components

In some embodiments of the present invention, the analyte molecules may immobilized with respect to a surface (e.g., the surface of a capture object, the surface of a location (e.g., reaction vessel), or the like). The analyte molecules may be immobilized with respect to a surface prior to or following exposure to a plurality of types of binding ligands. In some embodiments, immobilization of the analyte molecules with respect to a surface may aid in removal of any excess binding ligands from the solution without concern of dislodging the analyte molecule from the surface (e.g., from the reaction vessel). Generally, a capture component allows the attachment of a molecule, particle, or complex to a solid support (e.g., capture object, location, etc.) for the purposes of immobilization, detection, quantification, and/or other analysis of the molecule, particle, or complex.

As will be appreciated by those in the art, the composition of the capture component will depend on the composition of the analyte molecule. Capture components for a wide variety of target molecules are known or can be readily found or developed using known techniques. For example, when the target molecule is a protein, the capture components may comprise proteins, particularly antibodies or fragments thereof (e.g., antigen-binding fragments (Fabs), Fab' fragments, pepsin fragments, F(ab')$_2$ fragments, full-length polyclonal or monoclonal antibodies, antibody-like fragments, etc.), other proteins, such as receptor proteins, Protein A, Protein C, etc., or small molecules. In some cases, capture components for proteins comprise peptides. For example, when the target molecule is an enzyme, suitable capture components may include enzyme substrates and/or enzyme inhibitors. In some cases, when the target analyte is a phosphorylated species, the capture component may comprise a phosphate-binding agent. For example, the phosphate-binding agent may comprise metal-ion affinity media such as those describe in U.S. Pat. No. 7,070,921 and U.S. Patent Application No. 20060121544. In addition, when the target molecule is a single-stranded nucleic acid, the capture component may be a complementary nucleic acid. Similarly, the target molecule may be a nucleic acid binding protein and the capture component may be a single-stranded or double-stranded nucleic acid; alternatively, the capture component may be a nucleic acid-binding protein when the target molecule is a single or double stranded nucleic acid. Alternatively, as is generally described in U.S. Pat. Nos. 5,270,163, 5,475,096, 5,567,588, 5,595,877, 5,637,459, 5,683,867, 5,705,337, and related patents, nucleic acid "aptamers" may be developed for capturing virtually any target molecule. Also, for example, when the target molecule is a carbohydrate, potentially suitable capture components include, for example, antibodies, lectins, and selectins. As will be appreciated by those of ordinary skill in the art, any molecule that can specifically associate with a target molecule of interest may potentially be used as a capture component.

For certain embodiments, suitable target analyte molecule/capture component pairs can include, but are not limited to, antibodies/antigens, receptors/ligands, proteins/nucleic acid, nucleic acids/nucleic acids, enzymes/substrates and/or inhibitors, carbohydrates (including glycoproteins and glycolipids)/lectins and/or selectins, proteins/proteins, proteins/small molecules; small molecules/small molecules, etc. According to one embodiment, the capture components are portions (particularly the extracellular portions) of cell surface receptors that are known to multimerize, such as the growth hormone receptor, glucose transporters (particularly GLUT 4 receptor), and T-cell receptors and the target analytes are one or more receptor target ligands.

In a particular embodiment, the capture component may be attached to the surface via a linkage, which may comprise any moiety, functionalization, or modification of the binding surface and/or capture component that facilitates the attachment of the capture component to the surface. The linkage between the capture component and the surface may comprise one or more chemical or physical (e.g., non-specific attachment via van der Waals forces, hydrogen bonding, electrostatic interactions, hydrophobic/hydrophilic interactions; etc.) bonds and/or chemical linkers providing such bond(s). In certain embodiments, the capture component comprises a capture extender component. In such embodiments, the capture component comprises a first portion that binds the analyte molecule and a second portion that can be used for attachment to the binding surface.

In certain embodiments, a surface may also comprise a protective or passivating layer that can reduce or minimize non-specific attachment of non-capture components (e.g., analyte molecules, binding ligands) to the binding surface during the assay which may lead to false positive signals during detection or to loss of signal. Examples of materials that may be utilized in certain embodiments to form passivating layers include, but are not limited to: polymers, such as poly(ethylene glycol), that repel the non-specific binding of proteins; naturally occurring proteins with this property, such as serum albumin and casein; surfactants, e.g., zwitterionic surfactants, such as sulfobetaines; naturally occurring long-chain lipids; and nucleic acids, such as salmon sperm DNA.

One embodiment utilizes proteinaceous capture components. As is known in the art, any number of techniques may be used to attach a proteinaceous capture component to a wide variety of solid surfaces. "Protein" or "proteinaceous" in this context includes proteins, polypeptides, peptides, including, for example, enzymes, and antibodies. A wide variety of techniques are known to add reactive moieties to proteins, for example, the method outlined in U.S. Pat. No. 5,620,850. The attachment of proteins to surfaces is known, for example, see Heller, Acc. Chem. Res. 23:128 (1990), and many other similar references.

In some embodiments, the capture component (or binding ligand) may comprise Fab' fragments. The use of Fab' fragments as opposed to whole antibodies may help reduce non-specific binding between the capture component and the binding ligand. In some cases, the Fc region of a capture component (or binding ligand) may be removed (e.g., proteolytically). In some cases, an enzyme may be used to remove the Fc region (e.g., pepsin, which may produce F(ab')$_2$ fragments and papain, which may produce Fab fragments). In some instances, the capture component may be attached to a binding surface using amines or may be modified with biotin (e.g., using NHS-biotin) to facilitate binding to an avidin or streptavidin coated capture object surface. F(ab')$_2$ fragments may be subjected to a chemical reduction treatment (e.g., by exposure to 2-mercaptoethylamine) to, in some cases, form two thiol-bearing Fab' fragments. These thiol-bearing fragments can then be attached via reaction with a Michael acceptor such as maleimide. For example, the Fab' fragments may then be treated with a reagent (e.g., maleimide-biotin) to attach at least one biotin moiety (i.e., biotinylated) to facilitate attachment to streptavidin-coated surfaces as described above.

Certain embodiments utilize nucleic acids as the capture component, for example for when the analyte molecule is a nucleic acid or a nucleic acid binding protein, or when the it is desired that the capture component serve as an aptamer for binding a protein, as is well known in the art.

According to one embodiment, each binding surface comprises a plurality of capture components. The plurality of capture components, in some cases, may be distributed randomly on the binding surface like a "lawn." Alternatively, the capture components may be spatially segregated into distinct region(s) and distributed in any desired fashion.

Binding between the capture component and the analyte molecule, in certain embodiments, is specific, e.g., as when the capture component and the analyte molecule are complementary parts of a binding pair. In certain such embodiments, the capture component binds both specifically and directly to the analyte molecule. By "specifically bind" or "binding specificity," it is meant that the capture component binds the analyte molecule with specificity sufficient to differentiate between the analyte molecule and other components or contaminants of the test sample. For example, the capture component, according to one embodiment, may be an antibody that binds specifically to some portion of an analyte molecule (e.g., an antigen). The antibody, according to one embodiment, can be any antibody capable of binding specifically to an analyte molecule of interest. For example, appropriate antibodies include, but are not limited to, monoclonal antibodies, bispecific antibodies, minibodies, domain antibodies, synthetic antibodies (sometimes referred to as antibody mimetics), chimeric antibodies, humanized antibodies, antibody fusions (sometimes referred to as "antibody conjugates"), and fragments of each, respectively. As another example, the analyte molecule may be an antibody and the capture component may be an antigen.

According to one embodiment in which an analyte particle is a biological cell (e.g., mammalian, avian, reptilian, other vertebrate, insect, yeast, bacterial, cell, etc.), the capture component may be a ligand having specific affinity for a cell surface antigen (e.g., a cell surface receptor). In one embodiment, the capture component is an adhesion molecule receptor or portion thereof, which has binding specificity for a cell adhesion molecule expressed on the surface of a target cell type. In use, the adhesion molecule receptor binds with an adhesion molecule on the extracellular surface of the target cell, thereby immobilizing or capturing the cell. In one embodiment in which the analyte particle is a cell, the capture component is fibronectin, which has specificity for, for example, analyte particles comprising neural cells.

In some embodiments, as will be appreciated by those of ordinary skill in the art, it is possible to detect analyte molecules using capture components for which binding to analyte molecules that is not highly specific. For example, such systems/methods may use different capture components such as, for example, a panel of different binding ligands, and detection of any particular analyte molecule is determined via a "signature" of binding to this panel of binding ligands, similar to the manner in which "electronic noses" work. This may find particular utility in the detection of certain small molecule analytes. In some embodiments, the binding affinity between analyte molecules and capture components should be sufficient to remain bound under the conditions of the assay, including wash steps to remove molecules or particles that are non-specifically bound. In some cases, for example in the detection of certain biomolecules, the binding constant of the analyte molecule to its complementary capture component may be between at least about $10^4$ and about $10^6$ M$^{-1}$, at least about $10^5$ and about $10^9$ M$^{-1}$, at least about $10^7$ and about $10^9$ M$^{-1}$, greater than about $10^9$ M$^{-1}$, or greater. For example, typical affinities for IgG antibodies for their antigens are in the range $10^5$-$10^{10}$ M$^{-1}$. The affinity of biotin for streptavidin is $10^{15}$ M$^{-1}$.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively.

What is claimed:

1. A method for determining a measure of the concentration of an analyte molecule or particle in a fluid sample, the method comprising:
    providing a fluid sample containing or suspected of containing a plurality of the analyte molecules or particles, each analyte molecule or particle comprising a first epitope and a second epitope;
    exposing the plurality of the analyte molecules or particles to a first type of binding ligand having an affinity for the first epitope on the analyte molecule or particle and a second type of binding ligand having an affinity for the second epitope on the analyte molecule or particle;
    forming a complex comprising the analyte molecule or particle associated with both the first type of binding ligand and the second type of binding ligand in addition to being associated with a capture object via a capture component;
    spatially separating at least a portion of the analyte molecules or particles into a plurality of locations, such that at least some of the plurality of locations contain at least one analyte molecule or particle and a statistically significant fraction of the plurality of locations do not contain any analyte molecules or particles;
    addressing at least a portion of the plurality of locations and determining the number of said locations containing both the first type of binding ligand and the second type of binding ligand; and
    determining a measure of the concentration of the analyte molecules or particles in the fluid sample based at least in part on the number of locations containing both the first type of binding ligand and the second type of binding ligand.

2. The method of claim 1, wherein the exposing step occurs prior to the spatially separating step.

3. The method of claim 1, wherein the spatially separating step occurs prior to the exposing step.

4. The method of claim 1, wherein the plurality of locations each comprise a binding surface having an affinity for the plurality of analyte molecules or particles.

5. The method of claim 4, further comprising immobilizing the portion of analyte molecules which were spatially separated into the plurality of locations with respect to the binding surface of the locations.

6. The method of claim 1, further comprising immobilizing the plurality of analyte molecules or particles to a plurality of discrete objects such that a statistically significant fraction of the discrete objects are immobilized with respect to only a single analyte molecule or particle and a statistically significant fraction of the discrete objects are free of any analyte molecules or particles, prior to the exposing and spatially separating steps.

7. The method of claim 1, wherein the first type of binding ligand and the second type of binding ligand are directly detected.

8. The method of claim 1, wherein the first type of binding ligand and the second type of binding ligand are indirectly detected.

9. The method of claim 1, wherein the first type of binding ligand comprises a first type of enzymatic component and the second type of binding ligand comprises a second type of enzymatic component.

10. The method of claim 1, further comprising exposing the plurality of locations to a plurality of a first type of precursor labeling agent and a second type of precursor labeling agent.

11. The method of claim 10, wherein the first type of precursor labeling agent is converted to a first type of labeling agent upon exposure to the first type of binding ligand and the second precursor labeling agent is converted to a second type of labeling agent upon exposure to the second type of binding ligand, wherein the first type of labeling agent is distinguishable from the second type of labeling agent.

12. The method of claim 11, wherein the presence of the first type of binding ligand in a location is determined by determining the presence of the first type of labeling agent in that location and the presence of the second type of binding ligand in a location is determined by determining the presence of the second type of labeling agent in that location.

13. The method of claim 1, further comprising exposing the plurality of analyte molecules to a third type of binding ligand.

14. The method of claim 13, wherein the third type of binding ligand associates with the first type of binding ligand and the second type of binding ligand, wherein said first type of binding ligand and said second type of binding ligand are immobilized with respect to a single analyte molecule.

15. The method of claim 13, wherein the presence of the first type of binding ligand and the second type of binding ligand in a location is determined by determining the presence of the third type of binding ligand in the location.

16. The method of claim 13, wherein a measure of the concentration of analyte molecules or particles in the fluid sample is based at least in part on the number of locations containing the third type of binding ligand.

17. The method of claim 13, further comprising exposing the plurality of analyte molecules or particles to a fourth type of binding ligand.

18. The method of claim 17, wherein the third type of binding ligand associates with the first type of binding ligand and the fourth type of binding ligand associates with the second type of binding ligand.

19. The method of claim 18, wherein the presence of the first type of binding ligand in a location is determined by determining the presence of the third type of binding ligand in that location and the presence of the second type of binding ligand in a location is determined by determining the presence of the fourth type of binding ligand in that location.

20. The method of claim 1, wherein the first epitope and the second epitope are the same.

21. The method of claim 1, wherein the first epitope and the second epitope are different.

22. The method of claim 1, wherein the number of said locations containing the first type of binding ligand and the second type of binding ligand are determined using optical techniques.

23. The method of claim 1, wherein the plurality of locations comprises a plurality of reaction vessels.

24. The method of claim 23, further comprising sealing the plurality of reaction vessels.

25. The method of claim 23, wherein the average volume of the plurality of reaction vessels is between about 10 attoliters and about 100 picoliters.

26. The method of claim 1, wherein the concentration of analyte molecules or particles in the fluid sample is less than about $50 \times 10^{-15}$ M.

27. The method of claim 1, wherein the measure of the concentration of analyte molecules or particles in the fluid sample is determined at least in part by comparison of a measured parameter to a calibration standard.

28. The method of claim 1, wherein the number of locations addressed in the addressing step is at least about 5% of the total number of locations.

29. The method of claim 1, wherein the analyte molecules or particles are proteins or nucleic acids.

30. The method of claim 1, further comprising performing at least one wash step.

* * * * *

UNITED STATES PATENT AND TRADEMARK OFFICE
CERTIFICATE OF CORRECTION

PATENT NO. : 9,678,068 B2  
APPLICATION NO. : 12/731135  
DATED : June 13, 2017  
INVENTOR(S) : David C. Duffy et al.

It is certified that error appears in the above-identified patent and that said Letters Patent is hereby corrected as shown below:

In the Specification

Line 12 Immediately after the section entitled "RELATED APPLICATIONS" and before the section entitled "FIELD OF THE INVENTION", please insert the following new section:

--STATEMENT REGARDING FEDERALLY SPONSORED RESEARCH OR DEVELOPMENT  
This invention was made with government support under contract R43CA133987 awarded by the National Cancer Institute. The government has certain rights in the invention.--

Signed and Sealed this  
First Day of August, 2017

Joseph Matal  
*Performing the Functions and Duties of the*  
*Under Secretary of Commerce for Intellectual Property and*  
*Director of the United States Patent and Trademark Office*